(12) United States Patent
Ji et al.

(10) Patent No.: US 12,419,592 B2
(45) Date of Patent: Sep. 23, 2025

(54) METHODS AND SYSTEMS FOR CT BALANCE MEASUREMENT AND ADJUSTMENT

(71) Applicant: SHANGHAI UNITED IMAGING HEALTHCARE CO., LTD., Shanghai (CN)

(72) Inventors: Min Ji, Shanghai (CN); Bing Li, Shanghai (CN); Yifeng Jiang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 402 days.

(21) Appl. No.: 17/816,724

(22) Filed: Aug. 1, 2022

(65) Prior Publication Data

US 2022/0378384 A1 Dec. 1, 2022

Related U.S. Application Data

(63) Continuation-in-part of application No. 16/920,790, filed on Jul. 6, 2020, now Pat. No. 11,399,781, which
(Continued)

(30) Foreign Application Priority Data

Dec. 25, 2015 (CN) .......................... 201510992334.6
Dec. 30, 2015 (CN) .......................... 201511024391.1

(51) Int. Cl.
*A61B 6/00* (2024.01)
*A61B 6/03* (2006.01)
(Continued)

(52) U.S. Cl.
CPC ................ *A61B 6/035* (2013.01); *A61B 6/03* (2013.01); *A61B 6/4435* (2013.01); *A61B 6/586* (2013.01);
(Continued)

(58) Field of Classification Search
None
See application file for complete search history.

(56) References Cited

U.S. PATENT DOCUMENTS

| 4,178,510 A | 12/1979 | Wagner |
| 6,171,243 B1 | 1/2001 | Gagnon et al. |

(Continued)

FOREIGN PATENT DOCUMENTS

| CN | 101329403 A | 12/2008 |
| CN | 102018524 A | 4/2011 |

(Continued)

OTHER PUBLICATIONS

International Search Report in PCT/CN2016/111816 mailed on Apr. 5, 2017, 8 pages.
(Continued)

*Primary Examiner* — Hoon K Song
(74) *Attorney, Agent, or Firm* — METIS IP LLC

(57) ABSTRACT

The present application discloses a method for detecting an abnormity in a ray source in a CT system, comprising obtaining scanning data obtained from at least two scans that are performed by a medical device, the medical device including a ray source configured to generate a plurality of rays and a detector configured to detect the plurality of rays; determining, based on a difference of the scanning data, a status characteristic index of the ray source; and determining whether abnormity exists in the ray source based on the status characteristic index.

19 Claims, 20 Drawing Sheets

Related U.S. Application Data is a continuation of application No. 15/773,990, filed as application No. PCT/CN2016/111816 on Dec. 23, 2016, now Pat. No. 10,702,221.

(51) Int. Cl.
| | | |
|---|---|---|
| *A61B 6/58* | (2024.01) | |
| *G01M 1/36* | (2006.01) | |
| *A61B 6/40* | (2024.01) | |
| *A61B 6/42* | (2024.01) | |

(52) U.S. Cl.
CPC ............... *G01M 1/36* (2013.01); *A61B 6/032* (2013.01); *A61B 6/037* (2013.01); *A61B 6/4035* (2013.01); *A61B 6/42* (2013.01); *A61B 6/447* (2013.01); *A61B 6/583* (2013.01)

(56) References Cited

U.S. PATENT DOCUMENTS

| | | |
|---|---|---|
| 2004/0199065 A1 | 10/2004 | Braunstein |
| 2004/0202283 A1 | 10/2004 | Okumura et al. |
| 2005/0199060 A1 | 9/2005 | Danz et al. |
| 2006/0229845 A1* | 10/2006 | Buttner .................. G01M 1/28 702/179 |
| 2007/0286332 A1 | 12/2007 | Gohno et al. |
| 2011/0200176 A1 | 8/2011 | Sharpless |
| 2012/0128123 A1 | 5/2012 | Goodenough et al. |
| 2012/0321036 A1* | 12/2012 | Nakanishi ............ A61B 6/5264 378/19 |
| 2015/0185107 A1 | 7/2015 | Lou et al. |
| 2020/0022669 A1 | 1/2020 | Ni et al. |

FOREIGN PATENT DOCUMENTS

| | | |
|---|---|---|
| CN | 102402787 A | 4/2012 |
| CN | 102772218 A | 11/2012 |
| CN | 102809464 A | 12/2012 |
| CN | 205181365 U | 4/2016 |
| CN | 205433722 U | 8/2016 |
| CN | 106918426 A | 7/2017 |
| CN | 106923852 A | 7/2017 |
| GB | 1540583 A | 2/1979 |
| JP | H07303636 A | 11/1995 |
| JP | 2002253546 A | 9/2002 |
| JP | 2009153920 A | 7/2009 |
| JP | 2010125116 A | 6/2010 |
| JP | 2011152255 A | 8/2011 |
| JP | 2013215352 A | 10/2013 |

OTHER PUBLICATIONS

First Office Action in Chinese Application No. 201510992334.6 mailed on Aug. 1, 2018, 9 pages.

Written Opinion in PCT/CN2016/111816 mailed on Apr. 5, 2017, 11 pages.

Gao, Yongsheng, Fault analysis of CT image ring artifacts, China Healthcare Frontiers, 3(18): 97, 2008.

Zhang, Weidong et al., Manifestation and Function checke of CT Images ring-fabricate, China Medical Equipment, 4(9): 53-56, 2007.

First Office Action in Chinese Application No. 201511024391.1 mailed on Mar. 31, 2021, 26 pages.

Chen, Xiao, Spectra on Phase Transistion of Ferroelectric Oxides and Physical Properties Measurement System, Chinese Doctor's Theses Full-text Database Engineering Science and Technology Series II, 2014, 119 pages.

\* cited by examiner

METHODS AND SYSTEMS FOR CT BALANCE MEASUREMENT AND ADJUSTMENT

CROSS REFERENCES

The present application is a continuation-in-part of U.S. application Ser. No. 16/920,790, filed on Jul. 6, 2020, which is a continuation of U.S. application Ser. No. 15/773,990, filed on Jun. 13, 2018, now U.S. Pat. No. 10,702,221, which is a U.S. national stage under 35 U.S.C. § 371 of International Application No. PCT/CN2016/111816, filed on Dec. 23, 2016, which claims priority of Chinese Patent Application No. 201511024391.1, filed on Dec. 30, 2015, and Chinese Patent Application No. 201510992334.6, filed on Dec. 25, 2015, the contents of each of which are hereby incorporated by reference in their entireties.

TECHNICAL FIELD

This present disclosure relates to CT (Computed Tomography), and more particularly, relates to methods for anomaly detection of optical paths and adjustment of dynamic balance.

BACKGROUND

Computed Tomography (CT) can scan a specific area of an object in a specific thickness using X-rays. Different human tissues in the specific area can have different absorptive capacities of X-ray. CT can produce cross-sectional images of the specific area by computer reconstruction.

The optical path in a CT system 100 can include one or more optical components, for example, a filter, a collimator, a detector, etc. The optical components can have a great influence on CT image quality. In order to make sure the optical components in normal work status, the optical components can be examined before the CT system starts working. The examination can include examining whether there is a fault and/or foreign object, whether there is a presence of tilt and/or insecurity, etc. The examination can need further operations of an operator. For example, examining whether there is a fault and/or foreign object in the filter and/or detector, can need much attention of the operator. Additionally, the examination, for example, examining whether there is a presence of the tilt of the filter and/or the insecurity of the collimator, can need accessory equipment.

In order to acquire high-quality images of a body and/or heart, the CT system 100 can reduce motion artifact by increasing the rotational speed of the gantry. Due to the inhomogeneous mass distribution (also referred to as dynamic imbalance) of the rotors of the gantry, the gantry can produce vibration under the high-speed rotation. The vibration can reduce the service life of the parts and/or bearings in the gantry, reduce image quality, produce noise, etc. Additionally, the mass distribution of each rotor of the gantry is different in the process of manufacture. There is a need to measure the status of the dynamic balance of the gantry and adjust the status of dynamic balance based on the measured status. The measure and adjustment can need human intervention. For example, the operator can measure and adjust the status of dynamic balance. The operations by the operator are inconvenient and inaccurate.

In summary, there may be desirable for a method for measuring and adjusting the status of dynamic balance with less human intervention, less expense, and/or more accuracy.

SUMMARY

An aspect of the present disclosure is a CT system. The system may include a gantry, the gantry includes a rotor configured to rotate; a ray source, the ray source is configured to generate a plurality of rays; a detector, the detector is configured to detect rays; a controller, in communication with the ray source, configured to control the gantry to perform a test scan along an optical path of the CT system, the optical path being a path along which the plurality of rays pass from the ray source to the detector; and a processor, in communication with the detector and the controller, configured to obtain data obtained from the test scan, determine a status characteristic index of the optical path or an amount of dynamic imbalance of the gantry based on the data relating to the test scan, analyze the status characteristic index or the amount of dynamic imbalance, and determine whether the optical path is abnormal based on a result of the analysis of the status characteristic index, or determine whether a dynamic balance of the gantry satisfies a requirement based on a result of the analysis of the amount of dynamic imbalance.

According to some embodiments of the present disclosure, to analyze the status characteristic index and to determine whether the optical path is abnormal based on the result of the analysis of the status characteristic index, the processor may be further configured to compare the status characteristic index with a standard characteristic index to generate a first comparison result; and determine whether the optical path is abnormal based on the first comparison result.

According to some embodiments of the present disclosure, to analyze the status characteristic index and to determine whether the optical path is abnormal based on the result of analyzing the status characteristic index, the processor may be further configured to determine whether one of a plurality of optical path components in the optical path is abnormal or a path between two of the plurality of optical path components is abnormal, the plurality of optical path components including the ray source, the detector, or a component between the ray source and the detector during the test scan.

According to some embodiments of the present disclosure, to determine whether one of the plurality of optical path components along the optical path is abnormal, the processor may be further configured to determine at least one of whether the one of the plurality of optical path components is defective; whether there is a foreign object in the optical path component; whether the optical path component vibrates; or whether the optical path component tilts.

According to some embodiments of the present disclosure, to determine whether a path between two of the plurality of optical path components is abnormal, the processor may be further configured to determine whether there is a foreign object in the path between the two of the plurality optical path components.

According to some embodiments of the present disclosure, the test scan includes a static scan or a rotating scan.

According to some embodiments of the present disclosure, the test scan includes a single-focal spot scan or a multi-focal spots scan.

According to some embodiments of the present disclosure, the controller is configured to control the gantry to perform at least two test scans along the optical path of the CT system, a first scanning condition under which a first test scan of the at least two test scans is perform is different from a second scanning condition under which a second test scan of the at least two test scans is performed, and the first scanning condition includes at least one of: a position of a focal spot of the ray source, energy of the plurality of rays, an object to be scanned, a rotating speed relating to a rotating scan, or a position of the ray source.

According to some embodiments of the present disclosure, the processor is further configured to determine the status characteristic index based on a difference in scanning data of the at least two test scans.

According to some embodiments of the present disclosure, the controller is further configured to control the gantry to perform at least two test scans along the optical path of the CT system, wherein, the at least two test scans share at least one scanning condition under which the at least two test scans are performed, the at least one scanning condition includes at least one of: a position of a focal spot of the ray source, energy of the plurality of rays, an object to be scanned, a rotating speed relating to a rotating scan, or a position of the ray source, and the processor is further configured to average scanning data of the at least two test scans.

According to some embodiments of the present disclosure, the object to be scanned is air or a phantom.

According to some embodiments of the present disclosure, the optical path component includes a filter, the controller is configured to control the gantry to perform a first test scan along the optical path of the CT system, and the processor is further configured to obtain scanning data of the first test scan; determine a status characteristic curved surface of the filter based on the scanning data of the first test scan; compare the status characteristic curved surface of the filter with a standard characteristic curved surface to generate a second comparison result; and determine whether the filter is defective or has a foreign object based on the second comparison result.

According to some embodiments of the present disclosure, the controller is further configured to control the gantry to perform a second test scan along the optical path of the CT system when the filter is not located in the optical path, and the processor is further configured to obtain scanning data of the second test scan; and determine the status characteristic curved surface of the filter based on a difference in the scanning data of the first test scan and the scanning data of the second test scan.

According to some embodiments of the present disclosure, the optical path component includes a filter; the controller is configured to control the gantry to perform a first test scan along the optical path of the CT system; and the processor is further configured to obtain scanning data of the first test scan, determine a status characteristic curved surface of the filter based on the scanning data of the first test scan, determine a parameter relating to a gravity center of the filter based on the status characteristic curved surface of the filter, compare the parameter relating to the gravity center of the filter with a standard parameter, and determine whether the filter tilts based on a result of the comparison.

According to some embodiments of the present disclosure, the controller is further configured to control the gantry to perform a second test scan along the optical path of the CT system when the filter is not located in the optical path, and the processor is further configured to obtain scanning data of the second test scan; and determine the status characteristic curved surface of the filter based on a difference in the scanning data of the first test scan and the scanning data of the second test scan.

According to some embodiments of the present disclosure, the optical path component includes a detector; the controller is configured to control the gantry to perform a first test scan along the optical path of the CT system; and the processor is further configured to obtain scanning data of the first test scan; determine a status characteristic curved surface of the detector based on the scanning data of the first test scan; compare the status characteristic curved surface of the detector with a standard characteristic curved surface to generate a third comparison result; and determine whether the detector is defective or has a foreign object based on the third comparison result.

According to some embodiments of the present disclosure, the controller is further configured to control the gantry to perform at least two first test scans along the optical path of the CT system, a first scanning condition under which a first test scan of the at least two test scans is performed different from a second scanning condition under which a second test scan of the at least two test scans is performed; and the processor is configured to determine the status characteristic curved surface of the detector based on scanning data of the at least two first test scans.

According to some embodiments of the present disclosure, the optical path component includes a collimator, the collimator comprising a blade; the controller is further configured to control the gantry to perform a first test scan along the optical path of the CT system; and the processor is further configured to obtain scanning data of the first test scan; determine an attenuation coefficient of the collimator based on the scanning data of the first test scan; compare the attenuation coefficient of the collimator with a standard attenuation coefficient; and determine whether the blade of the collimator tilts based on a result of the comparison.

According to some embodiments of the present disclosure, the controller is further configured to control the gantry to perform a second test scan along the optical path of the CT system when the collimator is not located in the optical path; and the processor is further configured to obtain scanning data of the second test scan; and determine the attenuation coefficient of the collimator based on a difference in the scanning data of the first test scan and the scanning data of the second test scan.

According to some embodiments of the present disclosure, the system may be further include a counterweight, the counterweight is positioned on the rotor of the gantry and is configured to move along an axial direction of the rotor.

According to some embodiments of the present disclosure, the processor is further configured to determine an amount of dynamic imbalance of the gantry based on the data of the test scan, and wherein the controller is further configured to adjust a position of the counterweight based on the amount of dynamic imbalance.

According to some embodiments of the present disclosure, the controller is configured to perform two test scans on a scanning phantom at a first rotating speed of the rotor and at a second rotating speed of the rotor, respectively; and wherein the processor is configured to obtain projection data of the two test scans, respectively; determine a difference in projection positions of the scanning phantom corresponding to the two test scans based on the projection data of the two test scans; and determine whether the dynamic balance of the gantry satisfies the requirement based on the difference in projection positions.

An aspect of the present disclosure is a method for detecting an abnormity in an optical path or measuring and adjusting of a dynamic balance of a gantry in a CT system. The method may include performing, by an gantry controlled by a controller, a test scan along an optical path of the CT system, the optical path being a path along which rays pass from a ray source to a detector; obtaining, by a processor, data relating to the test scan; determining, by the processor, a status characteristic index of the optical path or an amount of dynamic imbalance of the gantry based on the data relating to the test scan; analyzing, by the processor, the status characteristic index or the amount of dynamic imbalance; and determining, by the processor, whether the optical path is abnormal based on a result of the analysis of the status characteristic index, or determining whether a dynamic balance of the gantry satisfies a requirement based on a result of the analysis of the amount of dynamic imbalance.

According to some embodiments of the present disclosure, analyzing, by the processor, the status characteristic index and determining, by the processor, whether the optical path is abnormal based on the result of the analysis of the status characteristic index may include comparing the status characteristic index with a standard characteristic index to generate a first comparison result; and determining whether the optical path is abnormal based on the first comparison result.

According to some embodiments of the present disclosure, analyzing, by the processor, the status characteristic index and determining, by the processor, whether the optical path is abnormal based on the result of the analysis of the status characteristic index may include determining whether one of a plurality of optical path components in the optical path is abnormal or in a path between two of the plurality of optical path components is abnormal, the plurality of optical path components including the ray source, the detector, or a component between the ray source and the detector during the test scan.

According to some embodiments of the present disclosure, determining, by the processor, whether one of the plurality of optical path components in the optical path is normal includes determining at least one of whether the one of the plurality of optical path components is defective, whether there is a foreign object in the optical path component, whether the optical path component vibrates, or whether the optical path component tilts.

According to some embodiments of the present disclosure, determining whether a path between two of the plurality of optical path components is abnormal includes determining whether there is a foreign object in the path between the two of the plurality of optical path components.

According to some embodiments of the present disclosure, the test scan includes a static scan or a rotating scan.

According to some embodiments of the present disclosure, the test scan includes a single-focal spot scan or a multi-focal spots scan.

According to some embodiments of the present disclosure, the controller controls the gantry to perform at least two test scans along the optical path of the CT system, wherein a first scanning condition under which a first test scan of the at least two test scans is performed different from a second scanning condition under which a second test scan of the at least two test scans is performed, and the first scanning condition includes at least one of: a position of a focal spot of the ray source, energy of the plurality of rays, an object to be scanned, a rotating speed relating to a rotating scan, or a position of the ray source.

According to some embodiments of the present disclosure, the processor determines the status characteristic index based on a difference in scanning data of the at least two test scan.

According to some embodiments of the present disclosure, the controller controls the gantry to perform at least two test scan along the optical path of the CT system, wherein the at least two test scans share at least one scanning condition under which the at least two test scans are performed, and the at least one scanning condition includes at least one of: a position of a focal spot of the ray source, energy of the plurality of rays, an object to be scanned, a rotating speed relating to a rotating scan, or a position of the ray source, and the method further comprising averaging, by the processor, scanning data of the at least two test scans.

According to some embodiments of the present disclosure, the object to be scanned is air or a phantom.

According to some embodiments of the present disclosure, the gantry controlled by the controller performs a first test scan along the optical path of the CT system, wherein the component of the optical path includes a filter; the processor obtains scanning data of the first test scan; the processor determines a status characteristic curved surface of the filter based on the scanning data of the first test scan; the processor compares the status characteristic curved surface of the filter with a standard characteristic curved surface to generate a second comparison result; and the processor determines whether the filter is defective or has a foreign object based on the second comparison result.

According to some embodiments of the present disclosure, the gantry controlled by the controller performs a second test scan along the optical path of the CT system when the filter is not located in the optical path; the processor obtains scanning data of the second test scan; and the processor determines the status characteristic curved surface of the filter based on a difference in the scanning data of the first test scan and the scanning data of the second test scan.

According to some embodiments of the present disclosure, the gantry controlled by the controller performs a first test scan along the optical path of the CT system, wherein the component of the optical path includes a filter; the processor obtains scanning data of the first test scan; the processor determines a status characteristic curved surface of the filter based on the scanning data relating to the first test scan; the processor obtains a gravity center related parameter of the filter based on the status characteristic curved surface of the filter; the processor compares the gravity center related parameter of the filter with a standard gravity center related parameter to generate a parameter comparison result; and the processor determines whether the filter tilts based on the parameter comparison result.

According to some embodiments of the present disclosure, the gantry controlled by the controller performs a second test scan along the optical path of the CT system when the filter is not located in the optical path; the processor obtains scanning data of the second test scan; and the processor determines the status characteristic curved surface of the filter based on a difference in the scanning data of the first test scan and the scanning data of the second test scan.

According to some embodiments of the present disclosure, the gantry controlled by the controller performs a first test scan along the optical path of the CT system, the component of the optical path including a detector; the processor obtains scanning data of the first test scan; the processor determines a status characteristic curved surface of the detector based on the scanning data of the first test scan; the processor compares the status characteristic curved surface of the detector with a standard characteristic curved surface to generate a third comparison result; and the processor determines whether the detector is defective or has a foreign object based on the third comparison result.

According to some embodiments of the present disclosure, the gantry controlled by the controller performs at least two first test scan along the optical path of the CT system, a first scanning condition under which a first test scan of the at least two first test scans is perform being different from a second scanning condition under which a second test scan of the at least two first test scans is performed; and the processor determines the status characteristic curved surface of the detector based on scanning data of the at least two first test scan.

According to some embodiments of the present disclosure, the gantry controlled by the controller performs a first test scan along the optical path of the CT system, the component of the optical path including a collimator and the collimator including a blade; the processor obtains scanning data of the first test scan; the processor determines an attenuation coefficient of the collimator based on the scanning data of the first test scan; the processor compares the attenuation coefficient of the collimator with a standard attenuation coefficient; and the processor determines whether the blade of the collimator tilts based on the result of the comparison.

According to some embodiments of the present disclosure, the gantry controlled by the controller performs a second test scan along the optical path of the CT system when the collimator is not located in the optical path; the processor obtains scanning data of the second test scan; and the processor determines the attenuation coefficient of the collimator based on a difference in the scanning data of the first test scan and the scanning data of the second test scan.

According to some embodiments of the present disclosure, the method further includes adjusting the dynamic balance of the gantry based on the amount of dynamic imbalance.

According to some embodiments of the present disclosure, the gantry further includes a counterweight, wherein the counterweight is configured to move along an axial direction of the gantry, and wherein adjusting the dynamic balance of the gantry based on the amount of dynamic imbalance includes adjusting a position of the counterweight based on the amount of dynamic imbalance.

According to some embodiments of the present disclosure, the gantry controlled by the controller performs a test scan along the optical path of the CT system includes performing at least two test scans on a phantom in different scanning conditions.

According to some embodiments of the present disclosure, the processor sets a difference in projection positions of the phantom corresponding to the at least two test scans as the amount of dynamic imbalance.

According to some embodiments of the present disclosure, the controller performs two test scans on a scanning phantom at a first rotating speed of the rotor and at a second rotating speed of the rotor, respectively; the processor obtains projection data of the two test scans, respectively; the processor determines a difference in projection positions of the phantom corresponding to the two test scans; and the processor determines whether the dynamic balance of the gantry satisfies the requirement based on the difference in projection positions.

According to some embodiments of the present disclosure, the phantom is a regularly shaped object.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
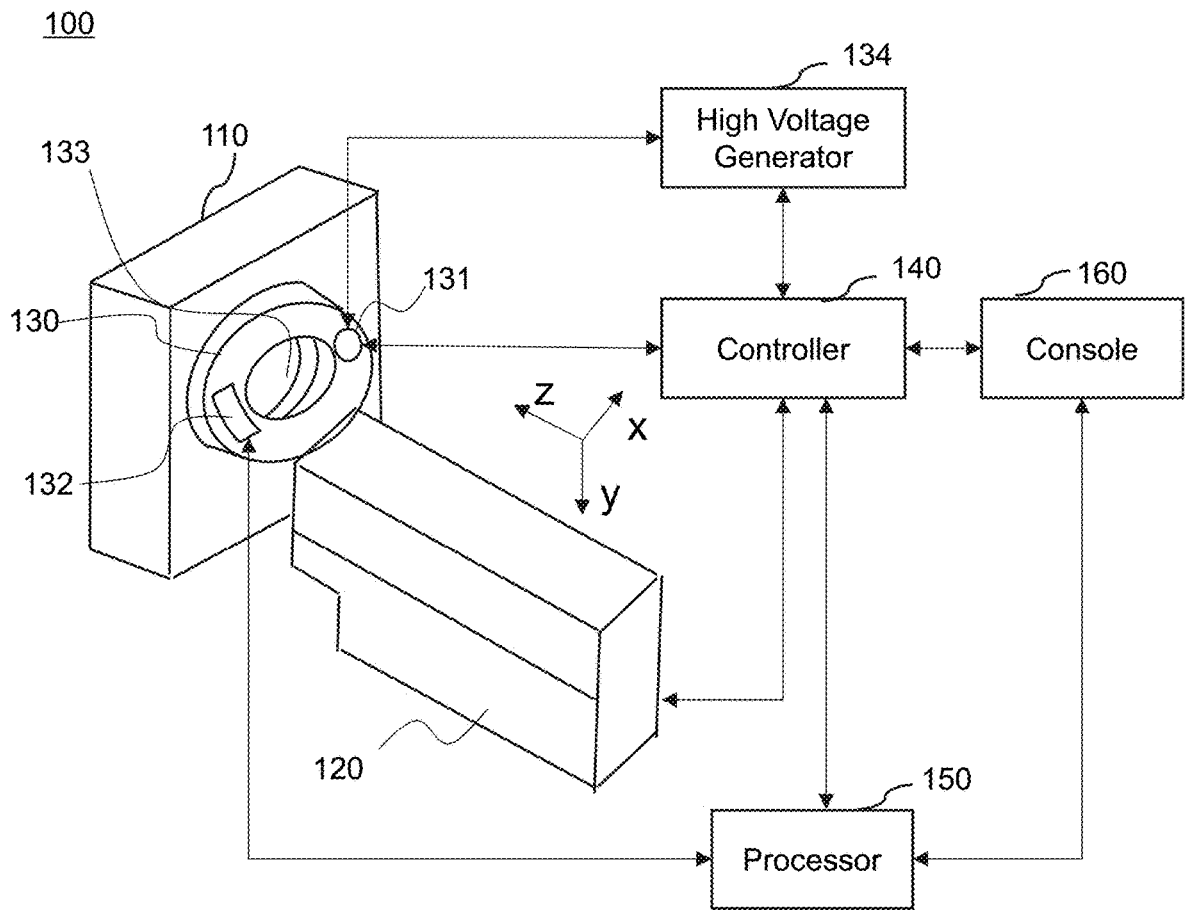
FIG. 1 shows an exemplary overall structure of a CT system according to some embodiments of the present disclosure.

To describe technical solutions in the embodiments of the present application more clearly, accompanying drawings required for describing the embodiments may be briefly introduced below. It is apparent that the drawings in the following description are merely some embodiments of the disclosure, and to those of ordinary skill in the art, the present disclosure may be applied to other similar scenarios according to these drawings without making creative efforts. Unless it is obvious from the language context or otherwise indicated, the same reference numerals represent the same structure or operation.

In the present specification and claims, the singular forms "a," "an," and "the" may be intended to include the plural forms as well, unless the context clearly indicates otherwise. Generally, terms "comprise" and "include," etc. may only mean including the operations and elements that have been explicitly identified, such operations and elements do not constitute an exclusive list, and a method or a device may also include other steps or elements.

Although the present application makes various references to certain modules in systems in some embodiments of the present application, any number of different modules may be used and implemented on the imaging system and/or processor. The modules are merely for illustration, and different aspects of the systems and methods may use different modules.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

According to some embodiments of the present application, FIG. 1 shows an overall structure of a CT system 100. As shown in FIG. 1, the CT system 100 may include a gantry 110, an examining table 120, a rotor 130, a ray source 131, a detector 132, a scanning chamber 133, a high voltage generator 134, a controller 140, a processor 150, and a console 160.

In some embodiments, the rotor 130 may be configured on the gantry 110. In some embodiments, the rotor 130 may rotate about the scanning chamber 133. The scanning chamber 133 may have a cylindrical shape. In some embodiments, the rotation axis of the rotor 130 may coincide with the axis of the scanning chamber 133.

The examining table 120 may move along the Z-axis direction, and at least a part thereof may be configured to be pushed into the scanning chamber 133. The Z-axis of the CT system 100 is the coordinate axis parallel to the rotation axis of the rotor 130. In some embodiments, an object 201 to be scanned (not shown in FIG. 1 and shown in FIG. 2A) may be placed on the examining table 120. In some embodiments, the object 201 to be scanned may be a phantom or a patient. The phantom may be an object to be scanned by the CT system 100, and a scanning result thereof may indicate an optical path status or a dynamic balance of the gantry of the CT system 100. In some embodiments, the phantom may be a regular object of known shape, for example, a spherical steel ball.

The ray source 131 and the detector 132 may be respectively configured at two opposite ends of the rotor 130. The ray source 131 may emit rays R that impinge upon the object 201 to be scanned. The detector 132 may receive the rays R passing through the object 201 to be scanned to sample projection data and convert the detected rays R into data needed for a subsequent image reconstruction. In some embodiments, the ray source 131 may emit X-rays. The ray source 131 may rotate around the Z-axis, and the detector 132 may move with respect to the ray source 131. In some embodiments, a spiral scan may also be performed. During the spiral scan, the ray source 131 may generate a helical trajectory with respect to the object 201 to be scanned due to the continuous movement of the object 201 to be scanned along the Z-axis and simultaneous rotation of the ray source 131.

The high voltage generator 134 may provide power. In some embodiments, the high voltage generator 134 may be connected to the ray source 131. In some embodiments, the high voltage generator 134 may be mounted in the gantry 110. In some embodiments, the high voltage generator 134 may be mounted in the ray source 131. In some embodiments, the high voltage generator 134 may be separately mounted outside of the gantry 110. It should be understood that the exemplary embodiments according to the present application and descriptions thereof may illustrate the present application and do not limit the present application.

The controller 140 may control scanning processes, operations of components, and movements of the components in scanning processes. In some embodiments, the controller 140 may communicate with the examining table 120 to control the movement thereof in scanning processes. In some embodiments, the controller 140 may communicate with the ray source 131 to control scanning processes thereof. In some embodiments, the controller 140 may communicate with the high voltage generator 134 to control scanning processes of the ray source 131. In some embodiments, the controller 140 may communicate with the processor 150 and the console 160 to control operations of the components.

The processor 150 may obtain projection measurement data of the object to be scanned for subsequent process. In some embodiments, the processor 150 may communicate with the detector 132 and may obtain the projection measurement data of the object to be scanned from the detector 132 for subsequent process. In some embodiments, the subsequent process of the data may include, but is not limited to, processing the projection measurement data to obtain an image, image contrast adjustment, image saturation adjustment, image brightness adjustment, image tone adjustment, image reconstruction, and image enhancement. In some embodiments, the processor 150 may obtain data/instructions from memory, and the memory may be a read-only memory (ROM), a random-access memory (RAM), a cache (not shown), a hard disk, other storage devices or the like. For example, the processor 150 may obtain, from memory, an instruction of processing the projection measurement data to obtain an image. The processor 150 may obtain, from the memory, an instruction of adjusting one or more of the image contrast, image saturation, image brightness and image tone. The processor 150 may obtain, from the memory, an instruction of reconstructing or enhancing the image. In some embodiments, the processor 150 may include a plurality of sub-processors that may be used to implement different functions of the system. The read-only memory may be used to control and process power-on self-test of the system 100, control and process initialization of various functional modules in the system 100, control and process a driver of basic input/output of the system 100, or the like. In some embodiments, the read-only memory may be a programmable read-only memory (PROM), an erasable programmable read-only memory (EPROM), a one-time programmable read-only memory (OPTROM), or the like.

The console 160 may include a display and an input device, present a user interface, data and images to a user, and have an interactive function that can be operated by the user. In some embodiments, the display may be one or more of a liquid crystal display (LCD), a light emitting diode (LED) display, an organic light emitting diode (OLED) display, a cathode ray tube (CRT) display, a plasma display, a touchscreen and an analogue touch screen. In some embodiments, the input device may be one or more of a handwriting input device, an image input device, an audio input device, an electromagnetic wave input device, a gesture input device, and a motion input device.

In some embodiments, one or more of the controller 140, the processor 150, and the console 160 may be mounted outside of the gantry 110. In some embodiments, the console 160 may include part or all of the controller 140 and/or the processor 150. In some embodiments, the controller 140 and the processor 150 may transmit data relating to a detection process and/or a detection result to the console 160. In some embodiments, the console 160 may transmit user operation-related data to the controller 140 and/or the processor 150 to better detect the optical path status and the dynamic balance of the gantry of the CT system 100. It should be understood that the exemplary embodiments according to the present application and descriptions thereof may illustrate the present application and do not limit the present application. For example, in some embodiments, one or more of the controller 140, the processor 150, and the console 160 may be mounted onto the gantry 110.

Figure 2A:
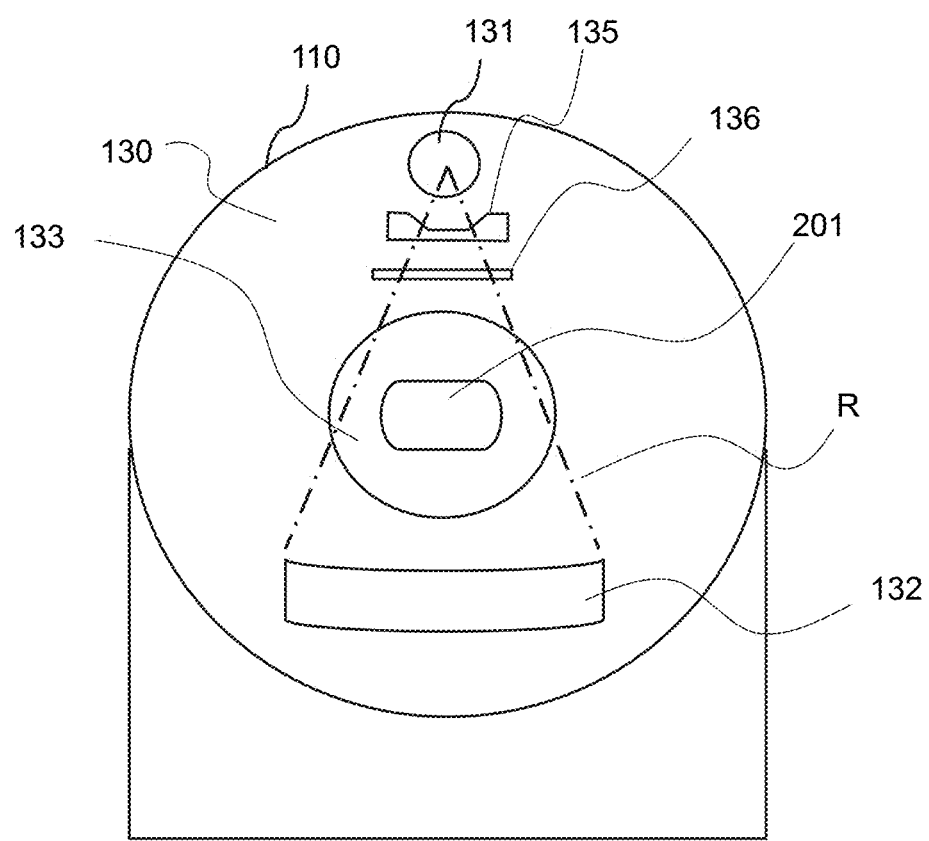
FIG. 2A shows an exemplary internal structure of a chamber of the CT system according to some embodiments of the present disclosure.

According to some embodiments of the present application, FIG. 2A shows an exemplary internal structure of a chamber of the CT system 100. As shown in FIG. 2A, the ray source 131, the detector 132, a filter 135, and a collimator 136 are configured on the rotor 130 of the CT system 100. The description of the ray source 131 and the detector 132 may refer to FIG. 1 and corresponding description thereof and are not further described here. The filter 135 and the collimator 136 may be sequentially configured on the rotor 130 and located between the ray source 131 and the object 201 to be scanned.

The collimator 136 may control an irradiation area of the rays R and further control a slice thickness of a part to be scanned of the object 201 to be scanned. In some embodiments, the collimator 136 may include a plurality of blades whose positions can be controlled. The collimator 136 may control the irradiation area of the rays R by controlling the positions of the blades.

The filter 135 may absorb low-energy rays of the rays R and may control irradiation intensity distribution of the rays R. In some embodiments, the rays may be X-rays. The low-energy rays are rays generated when a voltage between the cathode and anode of an X-ray generating element is less than a certain value. In some embodiments, the filter 135 may be configured between the ray source 131 and the collimator 136.

When the CT system 100 operates, X-rays emitted from the ray source 131 may pass through various components, for example, the filter 135, the collimator 136, and reach the detector 132. The path along which the rays pass from the ray source 131 to the detector 132 during a scan is referred to as an optical path. Performance of the device may be affected when the optical path is abnormal, for example when the detector 132 or the filter 135 is defective or has a foreign object, the filter 135 vibrates, or the collimator 136 tilts, or there is a foreign object between the components. The abnormality of the optical path, for example, an abnormal status of the detector 132, the filter 135, the collimator 136, or an area therebetween may be indicated by the data received by the detector 132 during the scan. Therefore, whether an abnormal status of the detector 132, the filter 135, the collimator 136, or an area therebetween exists may be determined by analyzing the data. For example, a status characteristic index for indicating whether the detector 132 or whether the filter 135 is defective or has a foreign object may be determined and characterized by a characteristic curved surface; a status characteristic index for indicating whether the filter 135 vibrates may be determined and characterized by a gravity center related parameter; a status characteristic index for indicating whether the collimator 136 tilts may be determined and characterized by an attenuation coefficient; or a status characteristic index may be determined for areas between the filter 135, the collimator 136, and the detector 132. In some embodiments, the status characteristic index may be an amount that can indicate a state of the optical path. In some embodiments, the status characteristic index may be a characteristic curved surface, a gravity center related parameter, or an attenuation coefficient. The characteristic curved surface may be a curved surface that indicates the distribution of irradiation intensity of the rays R controlled by the filter 135. The gravity center related parameter may be an amount that indicates the position of the gravity center of the filter 135. The attenuation coefficient may be an amount that indicates the control of the collimator 136 on the irradiation area of the rays R. Whether the components are abnormal may be determined by analyzing the status characteristic indexes of the detector 132, the filter 135, the collimator 136, and areas therebetween.

It should be noted that the above description of the internal structure of the chamber of the CT system 100 is merely for convenience of descriptions and is not intended to limit the present application to the scope of the embodiments. It should be understood that, for those skilled in the art, after understanding the principle of the system, it may be possible to combine the parts, connect a subsystem which is constituted by the parts with other parts, and amend and change configurations of the CT system 100 without departing from this principle. These amendments and changes are still within the scope of the above description. For example, in some embodiments, the detection of the status of the optical path is not limited to the determination of the above-described components, and other components in the optical path of the CT system 100 may also be used, as long as a status thereof may be indicated in the scanning data. Accordingly, the status characteristic index may be determined based on characteristics of the optical path components.

Figure 2B:
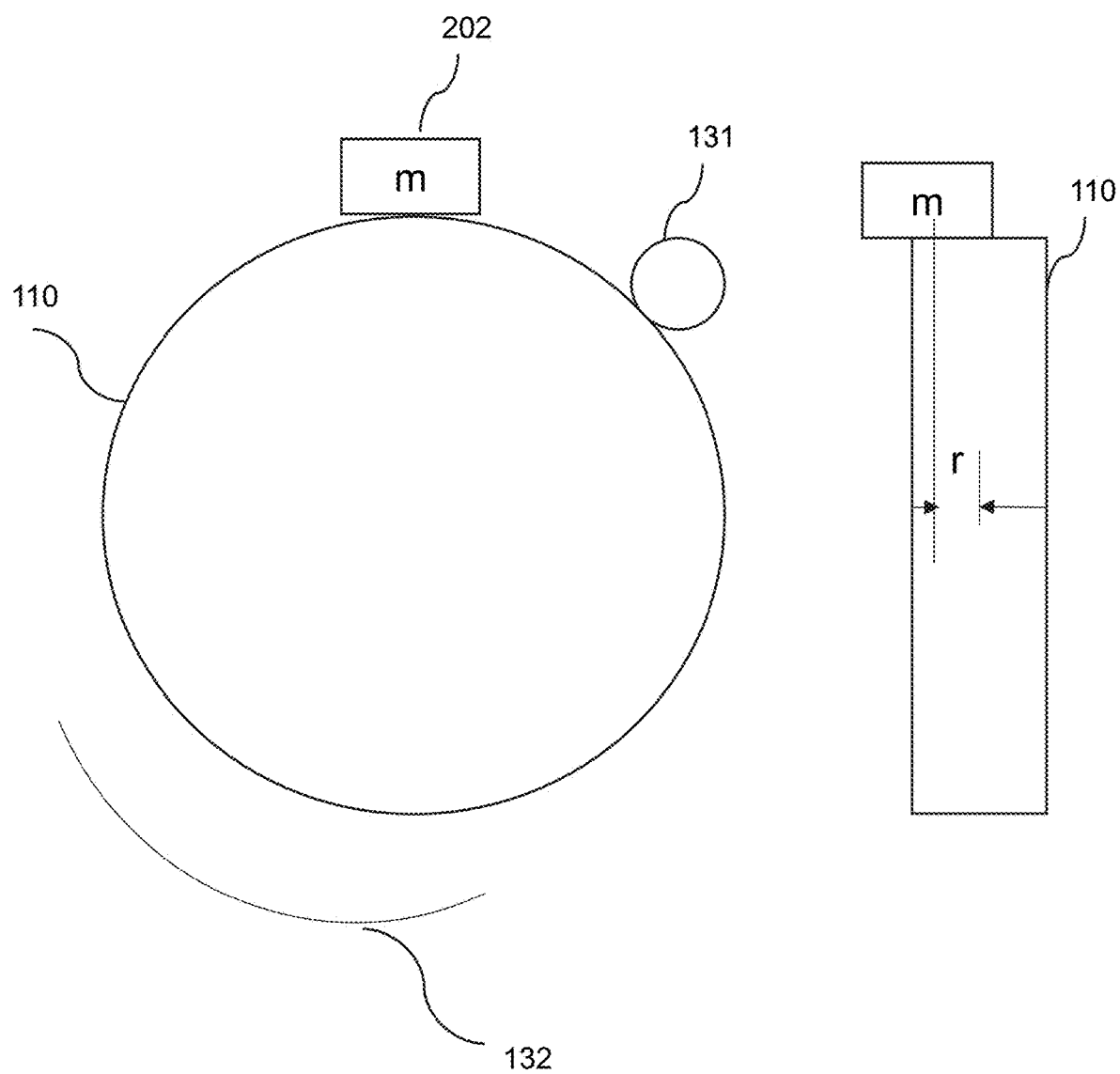
FIG. 2B shows an exemplary structure of the gantry of the CT system according to some embodiments of the present disclosure.

According to some embodiments of the present application, FIG. 2B shows an exemplary structure of the gantry 110 of the CT system 100. As shown in FIG. 2B, the ray source 131, the detector 132, and one or more counterweights 202 are configured on the rotor 130 of the gantry 110. For the convenience of descriptions, as shown in FIG. 2B, the weight of a counterweight 202 is m, and a distance by which the counterweight 202 moves is r when the position thereof is adjusted. In some embodiments, counterweight(s) 202 may ensure the static balance of the gantry 110. The static balance may be that the center of mass of the gantry 110 coincides with the center of rotation of the rotor 130. In some embodiments, the counterweight(s) 202 may also adjust the dynamic balance of the rotor 130 on the gantry 110. The above dynamic balance may need to be adjusted when there is a dynamic imbalance, in which case the rotor 130 on the gantry 110 may vibrate along the Z-axis of the CT system 100 when rotating. The dynamic imbalance may refer to a non-uniform mass distribution on the rotor 130. In some embodiments, an adjustment mode for the dynamic balance of the rotor 130 on the gantry 110 may be selected based on the weight m of a counterweight 202 and a fixing method thereof. In some embodiments, the above adjustment may include adjusting the position of the counterweight(s) 202 along the Z-axis direction. In some embodiments, the distance r by which the counterweight(s) 202 move when the position is adjusted may be determined by the following method based on results of two scans: assume that A is the deviation of projection positions corresponding to the two test scans and vibration of the rotor 130 of the gantry 110 during low-speed rotation test scan is zero; thus, the deviation Δ can be simplified as the deviation of projection position caused by vibration of the gantry 110 during high-speed rotation test scan:

$$\Delta = \frac{LR\omega^2 g}{Y}\cos(\omega t + \alpha) \qquad \text{Equation (1)}$$

In the Equation (1), Δ represents the deviation of projection positions corresponding to two test scans, Y represents stiffness of the gantry before and after the vibration, determined by the CT system 100 itself, R represents a distance between an imbalance amount and the center of rotation of the rotor (i.e., a radial distance between the gravity center of the counterweight(s) and the rotation axis of the rotor), t represents the time of the rotor rotating for a revolution, ω represents the angular speed of the high-speed rotation test scan, a represents the angle of the imbalance amount torque in the view direction (i.e., the phase of the counterweight(s) 202 during rotating), and L represents the imbalance amount torque.

The L and R can be obtained by the Fourier spectrum analysis based on the obtained differences between projection positions of the rotor rotating for a revolution at different view angles. Since the gravity center of a counterweight is adjustable in the mechanical design and the radial distance R of the rotation axis of the rotor is known, the imbalance amount torque L can be obtained. The imbalance amount torque L may be expressed as m*r, in which the mass m of the counterweight is known and the distance r by which the counterweight moves is equal to L/m.

It should be noted that the above description of the structure of the gantry 110 of the CT system 100 is merely for convenience of descriptions, and is not intended to limit the present application to the scope of the embodiments. It should be understood that, for those skilled in the art, after understanding the principle of the system, it may be possible to combine the parts, connect a subsystem which is constituted by the parts with other parts, and amend and change configurations of the CT system 100 without departing from this principle. These amendments and changes are still within the scope of the above description. Besides, it should be noted that the above adjustment mode for the dynamic balance of the gantry 110 is merely for convenience of descriptions, and is not intended to limit the present application to the scope of the embodiments. It should be understood that, for those skilled in the art, after understanding the principle of the method, it may be possible to amend and change the method without departing from this principle. These amendments and changes are still within the scope of the above description. For example, in some embodiments, the counterweight 202 may also move along other axes of the CT system 100 to adjust the dynamic balance. In some embodiments, the counterweight 202 may also move along a tangential direction of the rotor 130 to adjust the dynamic balance. In some embodiments, the distance by which the counterweight 202 moves may be determined based on one or more scanning results. In some embodiments, the distance by which the counterweight 202 moves may also be an average of a plurality of determination results.

Figure 3:
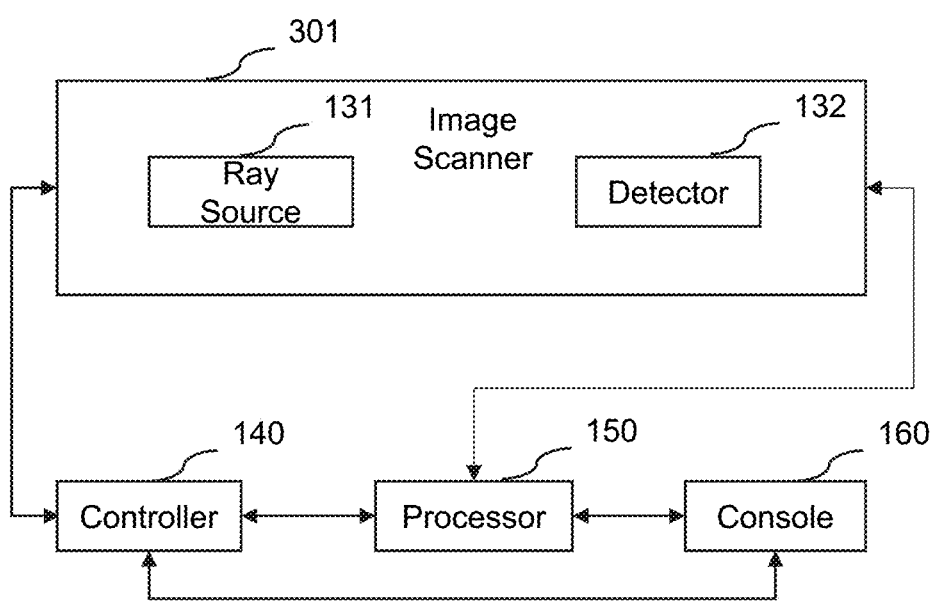
FIG. 3 shows exemplary devices of the CT system according to some embodiments of the present disclosure.

According to some embodiments of the present application, FIG. 3 shows exemplary devices of the CT system 100. As shown in FIG. 3, the CT system 100 may include an image scanner 301, the controller 140, the processor 150, and the console 160. The image scanner 301 may sample projection measurement data of the object 201 to be scanned and may include the ray source 131 and the detector 132. In some embodiments, the image scanner 301 may transmit data to the controller 140 and/or the processor 150. In some embodiments, the image scanner 301 may receive data from the controller 140 and/or the processor 150.

The controller 140 may be configured to perform test scans along the optical path of the CT system 100. The controller 140 may control scanning processes, including the process of test scans. In some embodiments, the controller 140 may communicate with the ray source 131. In some embodiments, the controller 140 also may communicate with the processor 150 and the console 160 to control operations of the two components.

The processor 150 may be configured to obtain data of the test scan, determine the status characteristic index of the optical path based on the data of the test scan, and analyze the status characteristic index to determine whether the optical path is abnormal. In some embodiments, the processor 150 may communicate with the detector 132 to obtain projection measurement data of the object 201 to be scanned for subsequent process.

The console 160 may present interfaces, data, and images to the user. In some embodiments, the console 160 may include a part or all of the controller 140 and/or the processor 150. In some embodiments, the controller 140 and/or the processor 150 may be inside the console 160. In some embodiments, the controller 140 and/or the processor 150 may be mounted on the outside of the console 160.

In some embodiments, the controller 140 and the processor 150 may perform specific detection operations according to different abnormity detections. For example, when detecting whether the detector 132 or the filter 135 is defective or has a foreign object, whether the filter 135 vibrates, or whether the collimator 136 tilts, the corresponding operations are performed. The details of the operations as well as other details of operations of the CT system 100 will be described in detail in the following embodiments and are not expanded here.

It should be noted that the above description of the exemplary structure of the CT system 100 is merely for convenience of descriptions, and is not intended to limit the present application to the scope of the embodiments. It should be understood that, for those skilled in the art, after understanding the principle of the system, it may be possible to combine the parts, connect a subsystem which is constituted by the parts with other parts, and amend and change configurations of the circuitry of the CT system 100 without departing from this principle. These amendments and changes are still within the scope of the above description. For example, in some embodiments, the console 160 may also communicate with the image scanner 301 or a part of the image scanner 301 to receive data of the image scanner 301 or the part thereof, and present the data to the user in the form of images, numbers, or texts.

Figure 4:
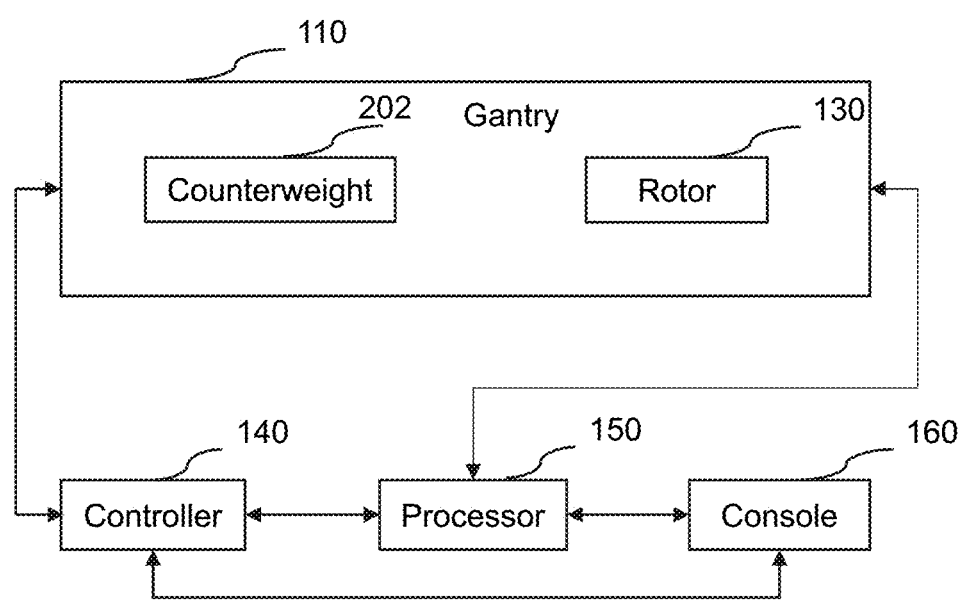
FIG. 4 shows an exemplary device of the CT system according to some embodiments of the present disclosure.

According to some embodiments of the present application, FIG. 4 shows an exemplary device of the CT system 100. As shown in FIG. 4, the CT system 100 may further include the gantry 110, and the gantry 110 may include the rotor 130, which may be rotatable, and the counterweight(s) 202 on the rotor 130. The counterweight(s) 202 may be configured to move along an axial (Z-axis) direction of the gantry 110 to adjust the dynamic balance of the gantry 110. Descriptions of the counterweight 202 and adjusting the dynamic balance of the gantry 110 by the counterweight 202 may refer to FIG. 1 and corresponding descriptions thereof, and details are not repeated here.

The controller 140 may be configured to control the gantry 110 to perform a test scan of the rotor 130, which may be rotatable. In some embodiments, the controller 140 may be connected to the gantry 110. The processor 150 may be configured to obtain scanning data of the test scan, determine an amount of dynamic imbalance based on the scanning data, and determine whether the dynamic balance status of the gantry 110 satisfies a requirement based on the amount of dynamic imbalance. In some embodiments, the processor 150 may be connected to the gantry 110 and the controller 140 separately.

In some embodiments, the controller 140 and the processor 150 may also be configured to adjust the position of the counterweight(s) 202. The processor 150 may obtain the amount of dynamic imbalance, and the controller 140 may adjust the position of the counterweight(s) 202 based on the amount of dynamic imbalance. Further, the controller 140 may be configured to perform a low-speed test scan and a high-speed test scan on the object 201 to be scanned. The processor 150 may be configured to obtain projection data of the two test scans respectively, determine the difference in projection positions of the object 201 to be scanned corresponding to the two test scans based on the projection data of the two test scans, and determine whether the dynamic balance of the gantry satisfies a requirement based on the difference in projection positions. Ideally, projection trajectories of the object 201 to be scanned should conform to a simple geometric model. Since the object 201 to be scanned remains still when the gantry vibrates, the projection trajectory deviates from the ideal geometric model, and the deviation may be used as an input parameter to the vibration model to obtain a vibration status and a corresponding imbalance amount of the gantry 110. In this way, manual operations and additional components are not needed, the workflow is simplified, the cost is reduced, and the result is more reliable.

The console 160 may be configured to provide a feedback as to whether the amount of dynamic imbalance satisfies a requirement or provide a feedback regarding the position of the counterweight(s) 202 that needs to be adjusted to the user, and the user may perform further adjustment through the control of the console 160. In some embodiments, the console 160 may be connected to the controller 140 and the processor 150 separately.

It should be noted that the above description of the exemplary structure of the CT system 100 is merely for convenience of descriptions, and is not intended to limit the present application to the scope of the embodiments. It should be understood that, for those skilled in the art, after understanding the principle of the system, it may be possible to combine the parts, connect a subsystem which is constituted by the parts with other parts, and amend and change configurations of the circuitry of the CT system 100 without departing from this principle. These amendments and changes are still within the scope of the above description. For example, in some embodiments, the console 160 may also communicate with the gantry 110 or a part of the gantry 110 to receive data of the gantry 110 or the part thereof, and present the data to the user in the form of images, numbers, or texts. It should be noted that the above description of the test scan is merely for convenience of descriptions, and is not intended to limit the present application to the scope of the embodiments. It should be understood by those skilled in the art that, after understanding the principle of the system, the method can be amended and changed without departing from the principle. For example, in some embodiments, other scanning conditions may be set, for example, performing two test scans with different rotor eccentricity to obtain an amount of dynamic imbalance, or using other scanning data other than the projection data (deviation of the projection positions) to obtain (or represent) an amount of dynamic imbalance of the gantry 110. Then, other vibration models are determined. Further, a mode in which the counterweight(s) 202 needs to be adjusted and an amount that needs to be adjusted may be obtained. The present application is not limited thereto.

Figure 5:
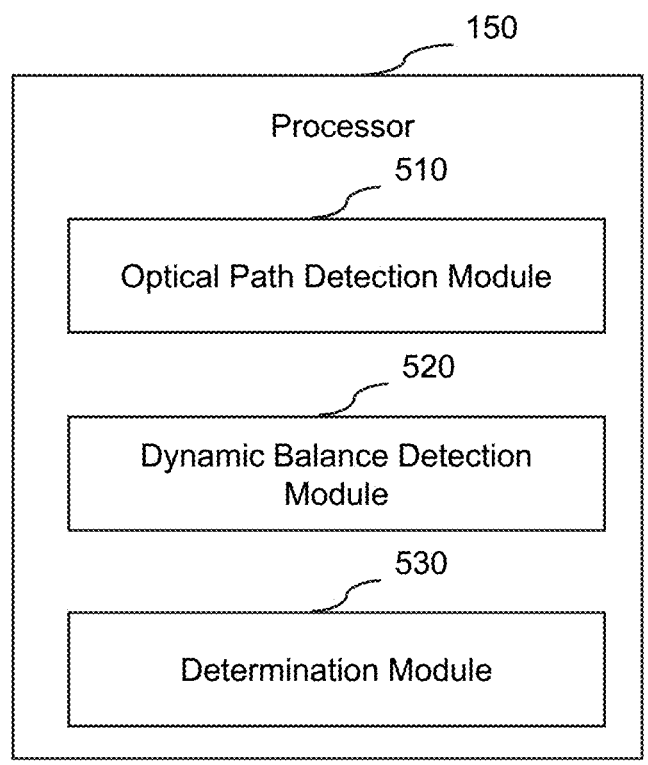
FIG. 5 shows an exemplary processor according to some embodiments of the present disclosure.

According to some embodiments of the present application, FIG. 5 shows an exemplary processor. The processor 150 may include the following modules: an optical path detection module 510, a dynamic balance detection module 520, and a determination module 530. It should be noted that the above description of the structure of the processor 150 is only exemplary and is not intended to limit the present application to the scope of the embodiments. In some embodiments, the processor 150 may also include other modules.

Generally, the words "module," "sub-module," "unit" and "sub-unit" in the present disclosure refer to a logical or a group of software instructions stored in hardware and firmware. The "module," "sub-module," "unit" and "sub-unit" herein may be implemented by software and/or hardware modules, or may be stored in any computer-readable non-transitory medium or another storage device. In some embodiments, a software module may be compiled and linked to an executable program. Obviously, the software module herein may respond to information transmitted by itself or other modules, and/or may respond when certain events or interruptions are detected. A software module configured to perform operations on a computing device (for example, processor 150) may be configured on a computer-readable medium. The computer-readable medium herein may be an optical disk, a digital optical disk, a flash disk, a magnetic disk or any other kind of tangible medium and the software module may also be obtained through a digital download mode (the digital download here may also include data stored in a compressed packet or an installation package that needs to be decompressed or decoded before being executed). The software code herein may be partially or all stored in a storage device of a computing device executing the operation and applied in the operation of the computing device. The software instructions may be embedded in firmware, for example, erasable programmable read-only memory (EPROM). Obviously, the hardware module may include connected logic units, for example, gates and triggers, and/or may include a programmable unit, for example, a programmable gate array or a processor. The functions of the modules or computing devices described herein are preferably implemented as software modules, but may also be represented in hardware or firmware. Normally, the module refers to a logical module and is not limited by a specific physical form or the memory. A module may be combined with other modules or divided into a series of sub-modules. In some embodiments, some of the above modules may not exist. In some embodiments, the above modules may be independent. In some embodiments, the above modules may be interrelated.

The optical path detection module 510 may detect the status of an optical path. The optical path is a path along which a plurality of rays of the CT system 100 pass from the ray source 131 to the detector 132. The detection of the status of the optical path may include detecting whether an optical component, for example, the detector 132, the filter 135, is defective or has a foreign object, whether the filter 135 vibrates or the collimator 136 tilts, or whether there is a foreign object in areas between optical components. In some embodiments, the above detection may be to scan air or the object 201 to be scanned once or more times. In some embodiments, the results detected by the optical path detection module 510 may be transmitted to the determination module 530.

The dynamic balance detection module 520 may detect the dynamic balance of the gantry. The detection of the dynamic balance of the gantry is to detect whether there is non-uniform mass distribution (dynamic imbalance) on the rotor 130 of the gantry. In some embodiments, the above detection may be to scan the object 201 to be scanned once or more times. In some embodiments, results detected by the dynamic balance detection module 520 may be transmitted to the determination module 530.

The determination module 530 may determine the data from the optical path detection module 510 and the dynamic balance detection module 520. The data from the optical path detection module 510 and the dynamic balance detection module 520 may be the detection results of the optical path status and the dynamic balance respectively. The data may include a status characteristic index, a value, a curve, an image, or the like. In some embodiments, the determination of the above method may be based on the status characteristic index. In some embodiments, the determination of the above method may be comparing the status characteristic index with a predetermined or detected standard value.

It should be noted that the above description of the processor 150 of the CT system 100 is merely for convenience of descriptions, and is not intended to limit the present application to the scope of the embodiments. It should be understood that, for those skilled in the art, after understanding the principle of the system, it may be possible to combine the modules, connect a subsystem which is constituted by the modules with other modules, and amend and change configurations of the processor 150 in the circuitry of the CT system 100 without departing from this principle. These amendments and changes are still within the scope of the above description. For example, in some embodiments, the processor 150 may further include one or more adjustment modules for adjusting the status of the optical path and/or the dynamic balance of the gantry. In some embodiments, the processor 150 may further include one or more storage modules to store data of the optical path detection module 510, the dynamic balance detection module 520, and the determination module 530.

Figure 6:
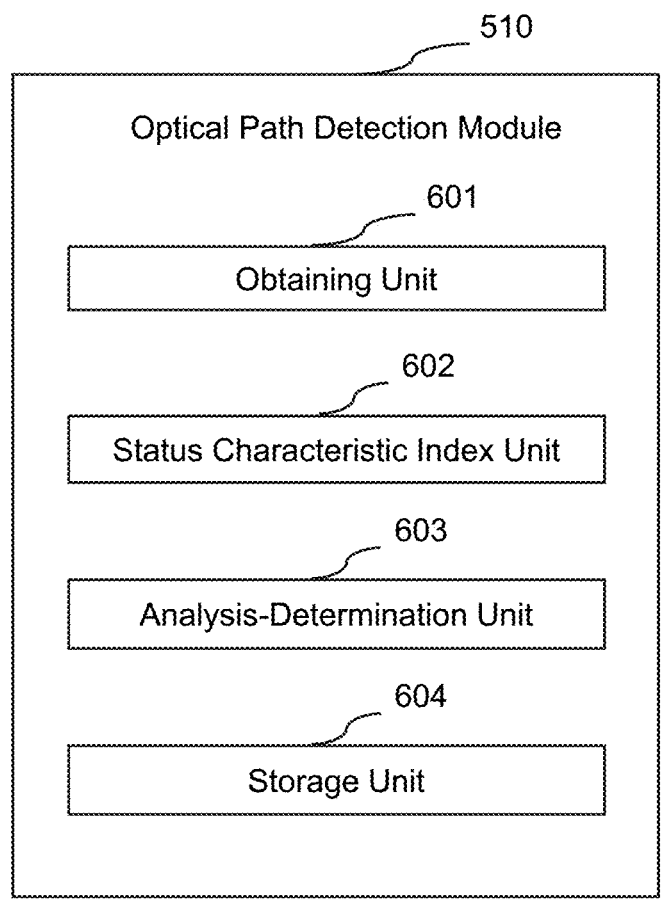
FIG. 6 shows an exemplary optical path detection module according to some embodiments of the present disclosure.

According to some embodiments of the present application, FIG. 6 shows an exemplary optical path detection module 510 in the processor 150. The optical path detection module 510 may include the following units: an obtaining unit 601, a status characteristic index unit 602, an analysis-determination unit 603, and a storage unit 604. It should be noted that the above description of the structure of the optical path detection module 510 is only exemplary and is not intended to limit the present application to the scope of the embodiments. In some embodiments, the optical path detection module 510 may also include other modules. In some embodiments, some of the above modules may not exist. In some embodiments, the above modules may be independent. In some embodiments, the above modules may be interrelated.

The obtaining unit 601 may obtain data obtained by the CT system 100 performing scans along an optical path. The scans may be to scan the air or the object 201 to be scanned along the optical path for once or more times. In some embodiments, the conditions of the scans may be the same or different. The data may include a value, a curve, an image, or the like. In some embodiments, the obtaining unit 601 may transmit the scanning data to the status characteristic index unit 602. In some embodiments, the obtaining unit 601 may also transmit the scanning data to the storage unit 604.

The status characteristic index unit 602 may determine the status characteristic index of the optical path based on the scanning data. The status characteristic index may include a status characteristic index (for example, a characteristic curved surface) indicating whether the detector 132 or the filter 135 is defective or has a foreign object, a status characteristic index (for example, a gravity center related parameter) indicating whether the filter 135 vibrates, a status characteristic index (for example, an attenuation coefficient) indicating whether the collimator 136 tilts, or a status characteristic index for areas between the filter 135, the collimator 136 and the detector 132. The determination process may include processing the scanning data, for example, a value or an image. In some embodiments, the determination process may be processing the scanning data corresponding to one or more scans. For example, the determination process may be subtracting or dividing the scanning data of the two scans. In some embodiments, the status characteristic index unit 602 may receive data from the obtaining unit 601. In some embodiments, the status characteristic index unit 602 may also receive data from the storage unit 604. In some embodiments, the status characteristic index unit 602 may transmit the determined status characteristic index to the analysis-determination unit 603.

The analysis-determination unit 603 may analyze and determine whether the optical path is abnormal. In some embodiments, the determination may be made based on the status characteristic index. In some embodiments, the determination may be made by comparing the status characteristic index with a standard characteristic index. In some embodiments, the analysis-determination unit 603 may receive data from the status characteristic index unit 602. In some embodiments, the analysis-determination unit 603 may receive data from the storage unit 604. In some embodiments, the analysis-determination unit 603 may transmit data to the storage unit 604. The storage unit 604 may store the data. The data may include a status characteristic index, a standard characteristic index, or the like. In some embodiments, the standard characteristic index may be a pre-stored standard characteristic index. In some embodiments, the standard characteristic index may be a standard characteristic index obtained by processing (for example, a smoothing operation) the scanning data once or more times in real time. The form of the data may include a value, a curve, an image, or the like.

It should be noted that the above description of the optical path detection module 510 of the processor 150 is merely for convenience of descriptions, and is not intended to limit the present application to the scope of the embodiments. It should be understood that, for those skilled in the art, after understanding the principle of the system, it may be possible to combine the units, connect a sub-unit which is constituted by the units with other units, and amend and change configurations of the optical path detection module 510 of the processor 150 in the circuitry of the CT system 100 without departing from this principle. These amendments and changes are still within the scope of the above description. For example, in some embodiments, the optical path detection module 510 may include a plurality of storage units. In some embodiments, each of the obtaining unit 601, the status characteristic index unit 602, and the analysis-determination unit 603 may correspond to a storage unit respectively.

Figure 7:
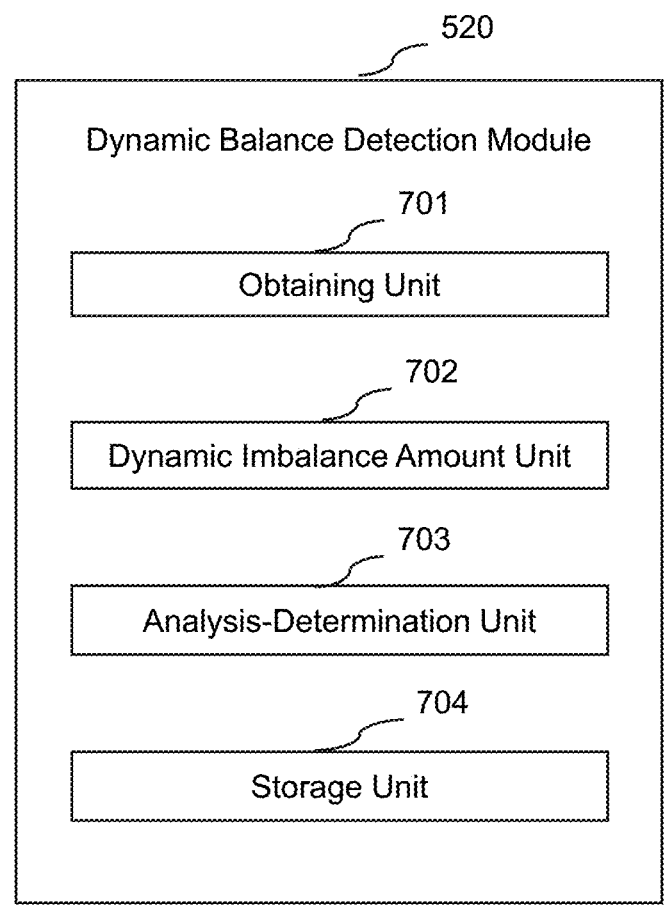
FIG. 7 shows an exemplary dynamic balance detection module according to some embodiments of the present disclosure.

According to some embodiments of the present application, FIG. 7 shows the dynamic balance detection module 520 in the processor 150. The dynamic balance detection module 520 may include the following units: an obtaining unit 701, a dynamic imbalance amount unit 702, an analysis-determination unit 703, and a storage unit 704. It should be noted that the above description of the structure of the dynamic balance detection module 520 is only exemplary and is not intended to limit the present application to the scope of the embodiments. In some embodiments, the dynamic balance detection module 520 may also include other modules. In some embodiments, some of the above modules may not exist. In some embodiments, the above modules may be independent. In some embodiments, the above modules may be interrelated.

The obtaining unit 701 may obtain the data obtained by the CT system 100 performing scans along the optical path. The scans may be to scan the object 201 to be scanned along the optical path twice. In some embodiments, the conditions of the two scans may be the same or different. The data may include a value, a curve, an image, or the like. In some embodiments, the obtaining unit 701 may transmit the scanning data to the dynamic imbalance amount unit 702. In some embodiments, the obtaining unit 701 may also transmit the scanning data to the storage unit 704.

The dynamic imbalance amount unit 702 may determine an amount of dynamic imbalance based on the scanning data. The determination process may include processing the scanning data, for example, a value, or an image. In some embodiments, the determination process may be subtracting or dividing the scanning data of the two scans. In some embodiments, the dynamic imbalance amount unit 702 may receive data from the obtaining unit 701. In some embodiments, the dynamic imbalance amount unit 702 may also receive data from the storage unit 704. In some embodiments, the dynamic imbalance amount unit 702 may transmit the determined status characteristic index to the analysis-determination unit 703.

The analysis-determination unit 703 may analyze and determine whether the dynamic balance of the gantry is abnormal. In some embodiments, the determination may be made based on the amount of dynamic imbalance. In some embodiments, the determination may be made by comparing the amount of dynamic imbalance with a standard amount of dynamic imbalance. In some embodiments, the analysis-determination unit 703 may receive data from the dynamic imbalance amount unit 702. In some embodiments, the analysis-determination unit 703 may receive data from the storage unit 704. In some embodiments, the analysis-determination unit 703 may transmit data to the storage unit 704. The storage unit 704 may store the data. The data may include an amount of dynamic imbalance, a standard amount of dynamic imbalance, or the like. The form of the data may include a value, a curve, an image, or the like.

It should be noted that the above description of the dynamic balance detection module 520 of the processor 150 of the CT system 100 for the gantry is merely for convenience of descriptions and is not intended to limit the present application to the scope of the embodiments. It should be understood that, for those skilled in the art, after understanding the principle of the system, it may be possible to combine the units, connect a sub-unit which is constituted by the units with other units, and amend and change configurations of the dynamic balance detection module 520 of the processor 150 in the circuitry of the CT system 100 for the gantry without departing from this principle. These amendments and changes are still within the scope of the above description. For example, in some embodiments, the dynamic balance detection module 520 for the gantry may include a plurality of storage units. In some embodiments, each of the obtaining unit 701, the dynamic imbalance amount unit 702 and the analysis-determination unit 703 may correspond to a storage unit respectively.

Figure 8:
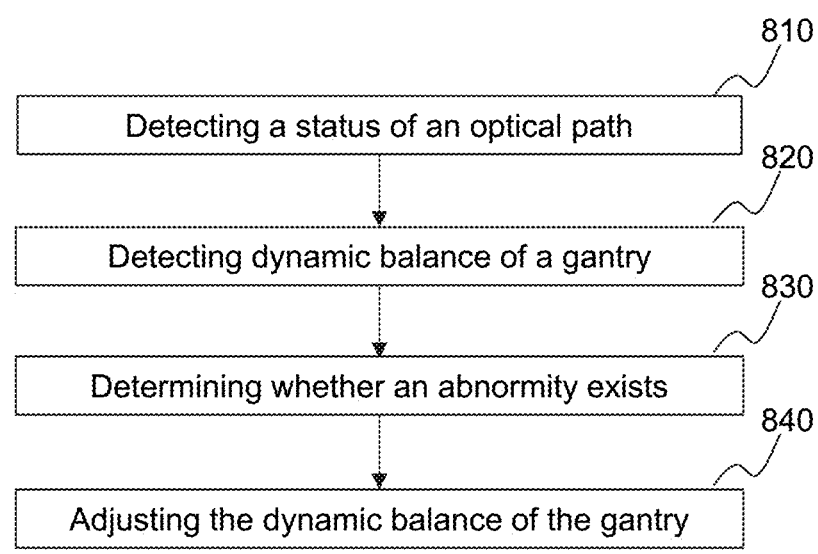
FIG. 8 shows the flowchart of an exemplary process for detecting the status of the optical path and the dynamic balance of the gantry according to some embodiments of the present disclosure.

According to some embodiments of the present application, FIG. 8 shows the flowchart of an exemplary process for detecting the status of the optical path and the dynamic balance of the gantry. As shown in FIG. 8, in step 810, the status of the optical path may be detected. In some embodiments, the optical path detection module 510 of the processor 150 may detect the status of the optical path. In some embodiments, the above detection may be to scan the air or the object 201 to be scanned for once or more times to obtain scanning data, and a status characteristic index is determined based on the scanning data. In some embodiments, the scanning conditions of the scans, for example, the position of a focal spot, energy, an object, a rotating speed relating to a rotating scan, the position of the ray source, or the like, may be the same or different.

In step 820, the dynamic balance of the gantry may be detected. In some embodiments, the dynamic balance detection module 520 of the processor 150 may detect the dynamic balance of the gantry. In some embodiments, the detection may be to scan the object 201 to be scanned for once or more times to obtain scanning data, and an amount of dynamic imbalance is determined based on the scanning data. In some embodiments, the scanning conditions of the scans, for example, the position of a focal spot, energy, an object, a rotating speed relating to a rotating scan, the position of the ray source, or the like, may be the same or different. In some embodiments, the one or more scans may be the one or more scans in step 810. In some embodiments, a part of the one or more scans may be the one or more scans in step 810. In some embodiments, the one or more scans may be different from the one or more scans in step 810.

In step 830, whether an abnormity exists may be determined. In some embodiments, the determination may be the status of an optical path and/or the dynamic balance of the gantry based on the status characteristic index and/or the amount of dynamic imbalance. In some embodiments, a standard value of the status characteristic index and/or a standard value of the amount of dynamic imbalance may be set or determined. In some embodiments, a deviation of the status characteristic index and/or the amount of dynamic imbalance may be obtained by comparing the status characteristic index and/or the amount of dynamic imbalance with a standard value thereof, to determine where the abnormity exists. In some embodiments, a threshold of the deviation of the status characteristic index and/or the amount of dynamic imbalance may be pre-determined. When the maximum deviation, the average deviation of the status characteristic index, and/or the amount of dynamic imbalance exceeds a corresponding threshold, the status of the optical path and/or the dynamic balance of the gantry may not satisfy a requirement. When the maximum deviation or the average deviation of the status characteristic index and/or the amount of dynamic imbalance does not exceed the corresponding threshold, the status of the optical path and/or the dynamic balance of the gantry may satisfy the requirement. In some embodiments, the threshold may include an upper threshold and a lower threshold. In some embodiments, the determination may be completed by the determination module 530.

In step 840, the dynamic balance of the gantry may be adjusted. In some embodiments, the dynamic balance of the gantry may be adjusted by adjusting the position of the counterweight(s) 202. In some embodiments, the user may determine whether to perform the adjustment or not. In some embodiments, the user may determine an amount of adjusting the position of the counterweight(s) 202. In some embodiments, the position of the counterweight(s) 202 may be adjusted by the controller 140. In some embodiments, the processor 150 may determine an adjustment mode and adjustment amount of the position of the counterweight(s) 202. In some embodiments, the processor 150 may determine the adjustment mode based on the weight m of a counterweight 202 and a fixing method thereof. In some embodiments, the above adjustment mode may include adjusting the position of the counterweight 202 along the Z-axis direction. In some embodiments, the processor 150 may determine the adjustment mode and adjustment amount of the position of the counterweight(s) 202 based on results of steps 820 and 830. In some embodiments, the adjustment amount is the distance r by which a counterweight 202 moves during the adjustment. In some embodiments, the movement distance r may be determined based on the deviation Δ of the projection positions corresponding to the two scans. For example, $$\Delta = \frac{LR\omega^2 g}{Y} \cos(\omega t + \alpha). \quad \text{Equation (1)}$$

In the Equation (1), Δ represents the deviation of projection positions corresponding to the two test scans, Y represents stiffness of the gantry before and after the vibration, determined by the CT system 100 itself, R represents a distance between an imbalance amount and the center of rotation of the rotor (i.e., the radial distance between the gravity center of the counterweight and the rotation axis of the rotor), t represents the time of the rotor rotating for a revolution, ω represents the angular speed of the high-speed rotation test scan, a represents the angle of the imbalance torque in the view direction (i.e., a phase of the counterweight 202 during rotating), and L represents the imbalance amount torque. The L and R can be obtained by a Fourier spectrum analysis based on the deviation Δ of the projection positions. Since the gravity center of the counterweight is adjustable in the mechanical design and the radial distance R of the rotation axis of the rotor is known, the imbalance amount torque L can be obtained. The imbalance amount torque L may be expressed as m*r, in which the mass m of the counterweight is known and the distance r by which the counterweight moves is equal to L/m.

It should be noted that the above description of the process for detecting the dynamic balance of the gantry and the status of the optical path of the CT system 100 is merely exemplary, and is not intended to limit the present application to the scope of the embodiments. It should be understood by those skilled in the art that, after understanding the process, various amendments and changes in forms and details of the application fields of implementing the above method and system may be realized while the function is realized, which is within the protection scope of the present application. For example, in some embodiments, the order of step 810 and step 820 is not fixed. For instance, in some embodiments, step 820 may be performed before step 810. In some embodiments, step 810 may be omitted. In some embodiments, step 820 may be omitted.

Figure 9:
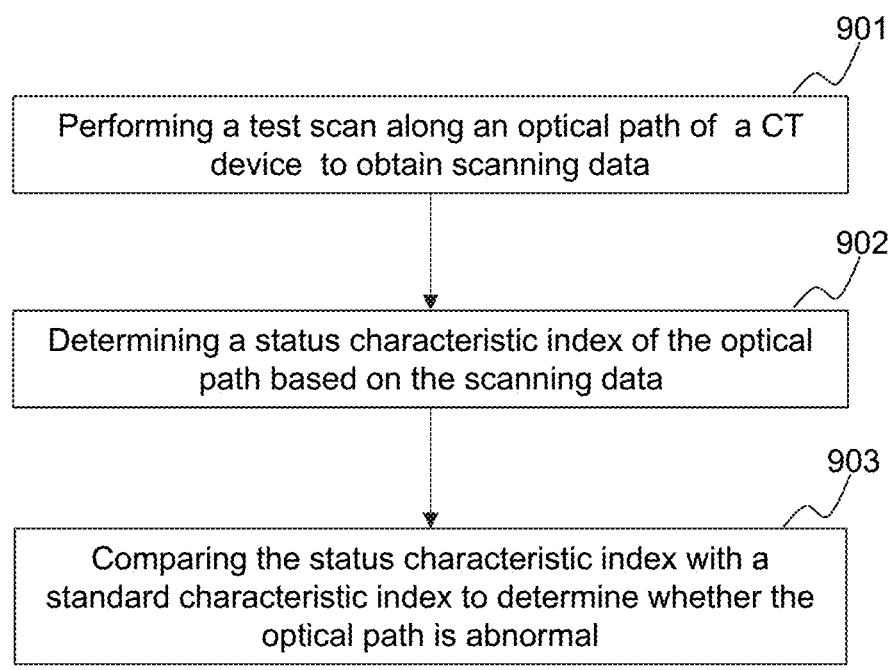
FIG. 9 shows the flowchart of an exemplary process for detecting the status of the optical path according to some embodiments of the present disclosure.

In some embodiments, in step 830, the detection of the status of the optical path (if the detection of the status of the optical path is performed) may be implemented by an exemplary process for detecting the abnormity of the optical path as shown in FIG. 9. As shown in FIG. 9, in step 901, a test scan may be performed along the optical path of the CT system 100 to obtain data of the test scan. In some embodiments, the controller 140 may control the ray source 131 to perform the test scan, and the obtaining unit 601 of the optical path detection module 510 may obtain the data of the test scan. Optical path components need to be located in the optical path during the scanning, which means the optical path components may affect the scanning data. For the filter 135 in FIG. 2A, when the filter 135 is located in the optical path, rays may pass through the filter 135 and reach the object 201 to be scanned, and therefore the signals detected by the detector 132 may be affected by the filter 135, and the effect will be represented in the scanning data converted by the detected signals. For the detector 132 in FIG. 2A, the detector 132 will be located in the optical path since it is a component needed to detect the signals. For the collimator 136 in FIG. 2A, the collimator 136 is located in the optical path if the rays are blocked by at least one blade of the collimator 136.

It should be noted that the number of times of scans may be once or more times here. In a case where multiple times of scans are performed, the scanning conditions may be the same or different. The scanning conditions may be the position of a focal spot, energy, an object, a rotating speed relating to a rotating scan, the position of the ray source, or the like. On one hand, the number of times may be determined based on reliability requirements. For example, comprehensive consideration on results on multiple scans under the same scanning conditions may increase the reliability of the scanning data and reduce unexpected interference. On the other hand, the number of times can be determined based on accuracy requirements. For example, comprehensive consideration of results of multiple scans under different scanning conditions may increase the accuracy or sensitivity of the scanning data. For instance, in conventional cases, only a single-focal spot scan is needed, but the accuracy or sensitivity of the scanning data may be increased by comparing scanning data obtained at different focal positions. In order to obtain data of different focal positions, a multi-focal spots scan may be performed, or a fly-focal spots scan may also be introduced. The energy is the energy of rays radiated by the ray source 131. An object may be the air (when the object 201 to be scanned is not placed on the examining table 120 in FIG. 1) or the object 201 to be scanned. When multiple scans are performed, a status characteristic index may be determined based on the differences between or among the data of the multiple scans. In some embodiments, a scanning mode may be a static scan or a rotating scan, which can be determined based on characteristics of the detection on the status of the optical path components. For example, both static scan and rotating scan may be suitable for a foreign object, defect or tilt detection.

In step 902, a status characteristic index of the optical path may be determined based on the data of the test scan(s). In some embodiments, the status characteristic index unit 602 of the optical path detection module 510 may determine the status characteristic index. The status characteristic index may characterize one aspect of the optical path components, for example, defects, foreign objects, vibrating, and tilting. For example, a characteristic curved surface determined for the detector 132 or the filter 135 may determine whether the components are defective or have a foreign object, a gravity center related parameter determined for the filter 135 may characterize whether the component vibrates, and an attenuation coefficient determined for the collimator 136 may characterize whether the component tilts.

In step 903, the status characteristic index may be analyzed to determine whether the optical path is abnormal. In some embodiments, the analysis-determination unit 603 of the optical path detection module 510 may determine the status characteristic index. The status characteristic index may characterize a status of a related optical path component, so that the related status of the optical path component may be determined by analyzing the index. For example, the status of an optical path component may include whether the optical path component is defective, has a foreign object, vibrates, or tilts.

Optionally, according to the embodiments of the present application, standard status characteristic indexes are pre-determined for normal statuses of the detector 132, the filter 135, and the collimator 136. For example, a standard status characteristic index for indicating that the detector 132 or the filter 135 is not defective and has no foreign object may be determined and characterized by a standard characteristic curved surface; a standard status characteristic index for indicating that the filter 135 does not vibrate may be determined and characterized by a relatively stable gravity center related parameter; or a standard status characteristic index for indicating that the collimator 136 does not tilt may be determined and characterized by a reasonable attenuation coefficient. It is possible to determine whether the components are abnormal by comparing the status characteristic indexes of the detector 132, the filter 135, and the collimator 136 with the standard status characteristic indexes thereof and calculating deviation degrees. The status characteristic index may further characterize a status of an area between related optical path components, so that the related status of the optical path may be determined by analyzing the index, for example, whether there is a foreign object in the area between the optical path components.

It should be noted that the above description of the process for detecting a status of the optical path of the CT system 100 is merely exemplary, and is not intended to limit the present application to the scope of the embodiments. It should be understood by those skilled in the art that, after understanding the process, various amendments and changes in forms and details of the application fields of implementing the above method and system may be realized while the function is realized, which is within the protection scope of the present application. For example, in some embodiments, the determination on whether an optical path component is abnormal may be completed only by analyzing a status characteristic index.

Figure 10:
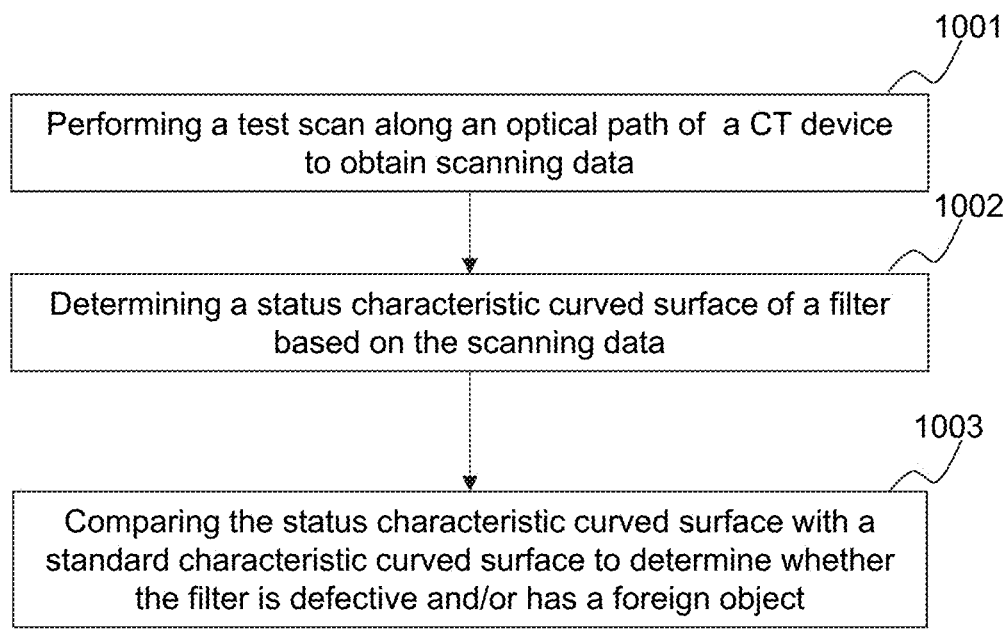
FIG. 10 shows the flowchart of an exemplary process for detecting whether a filter is defective or has a foreign object according to some embodiments of the present disclosure.

According to some embodiments of the present application, FIG. 10 shows the flowchart of an exemplary process for detecting whether a filter is defective or has a foreign object. As shown in the figure, in step 1001, one or more test scans may be performed along the optical path of the CT system 100 to obtain the data of the test scan(s). In some embodiments, a test scan with the filter is performed on the air, and then a test scan without the filter is further performed on the air. Scanning data of the two test scans is taken as first test scanning data. In some embodiments, the mode of the test scans may be a static scan or a rotating scan. In order to eliminate the error, the data of different test scans may be obtained by repeatedly performing test scans under different conditions, and the data of the test scans is comprehensively considered. For example, the CT system 100 may perform one or more test scans where the filter is not located in the optical path, to obtain second test scanning data.

In step 1002, a status characteristic curved surface of the filter may be determined based on the first test scanning data. In some embodiments, a status characteristic curved surface $L_1$ of the filter may be obtained by dividing the scanning data of the two test scans obtained in step 1001. In some embodiments, the status characteristic curved surface may be determined based on the difference between the first test scanning data and the second test scanning data. Those skilled in the art may also select other scanning conditions to obtain data of different test scans. Here, the difference may be determined by subtracting the scanning data of the two test scans or dividing the scanning data of the two test scans.

In step 1003, the status characteristic curved surface may be compared with a standard characteristic curved surface to determine whether the filter is defective and/or has a foreign object. In some embodiments, the status characteristic curved surface $L_1$ may be smoothed to obtain $L_1\_smooth$, and $L_1\_smooth$ is taken as the standard characteristic curved surface. Whether the filter is defective (or has a foreign object) is determined by comparing $L_1\_smooth$ and $L_1$. For example, whether the difference between $L_1\_smooth$ and $L_1$ (for example, $L_1\_smooth - L_1$) exceeds a threshold may be determined: if yes, the filter may be defective or may have a foreign object; and if no, the filter is not defective or may have no foreign object. In some embodiments, the threshold may include an upper threshold and a lower threshold.

In some embodiments, the comparison of the status characteristic curved surface and the standard characteristic curved surface may be performed by comparing each point on the status characteristic curved surface with each point on the standard characteristic curved surface, and whether the filter is defective or has a foreign object may be determined based on whether the difference corresponding to a point exceeds a threshold. In some embodiments, the threshold may include an upper threshold and a lower threshold. In some embodiments, the standard characteristic curved surface may also be obtained and stored in advance (for example, stored in the storage unit 604). For example, steps 1001 and 1002 may be performed in advance in a state where the filter is confirmed to be not defective and has no foreign object, and an obtained characteristic curved surface may be taken as the standard characteristic curved surface.

It should be noted that the above description of the process for detecting whether the filter of the CT system 100 is defective and/or has a foreign object is merely exemplary, and is not intended to limit the present application to the scope of the embodiments. It should be understood by those skilled in the art that, after understanding the process, various amendments and changes in forms and details of the application fields of implementing the above method and system may be realized while the function is realized, which is within the protection scope of the present application.

Figure 11:
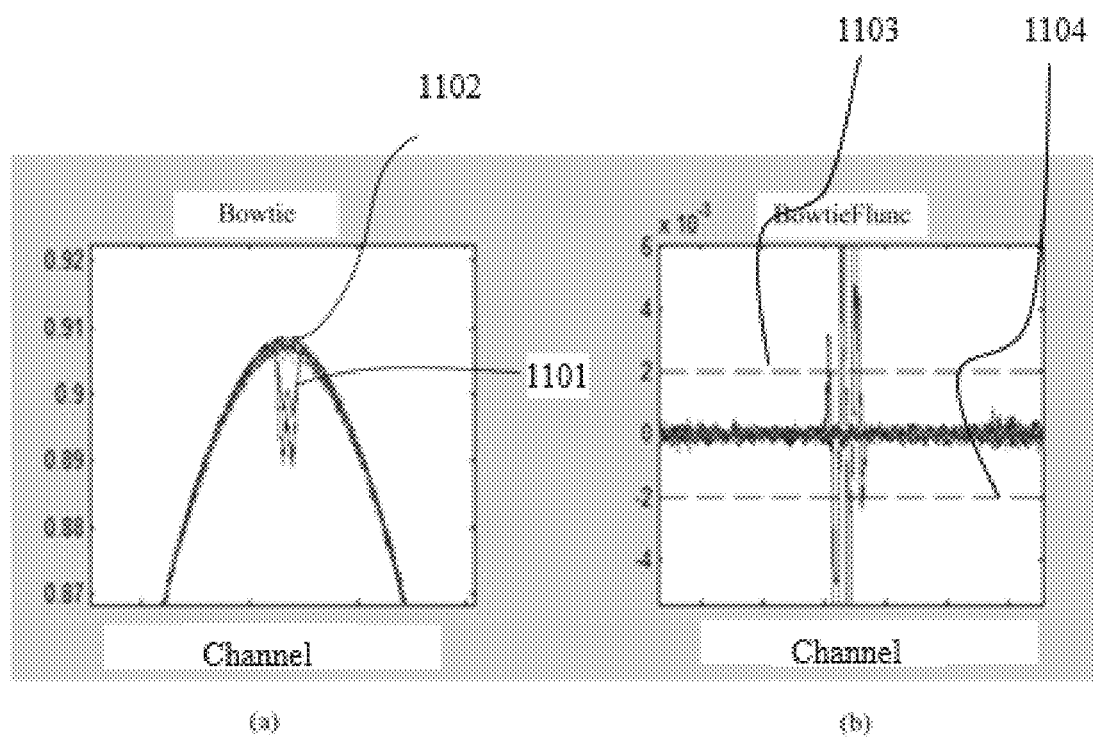
FIG. 11 shows exemplary experimental data obtained from examples of defect and foreign object detection for the filter according to some embodiments of the present disclosure.

FIGS. 11(a)-(b) are exemplary status characteristic curved surfaces obtained from examples of defect and foreign object detection for the filter of the CT system 100. The abscissa of FIG. 11 (a) represents individual channels of the detector, and the ordinate represents data obtained by dividing the scanning data of two test scans. 1101 is the status characteristic curved surface $L_1$ obtained by the test scan, and 1102 is the standard characteristic curved surface $L_1$_smooth. The ordinate of FIG. 11 (b) represents a value of $L_1$_smooth$-L_1$, and 1103 and 1104 are the upper threshold and lower threshold, respectively, for determining whether the filter is defective or has a foreign object respectively. As shown in FIG. 11, the status characteristic curved surface $L_1$ appears an image in the middle part when compared with the standard characteristic curved surface $L_1$_smooth, and if the value of mutation (for example, $L_1$_smooth$-L_1$) exceeds the upper limit 1103 or the lower limit 1104, it is determined that the filter is defective or has a foreign object.

Figure 12:
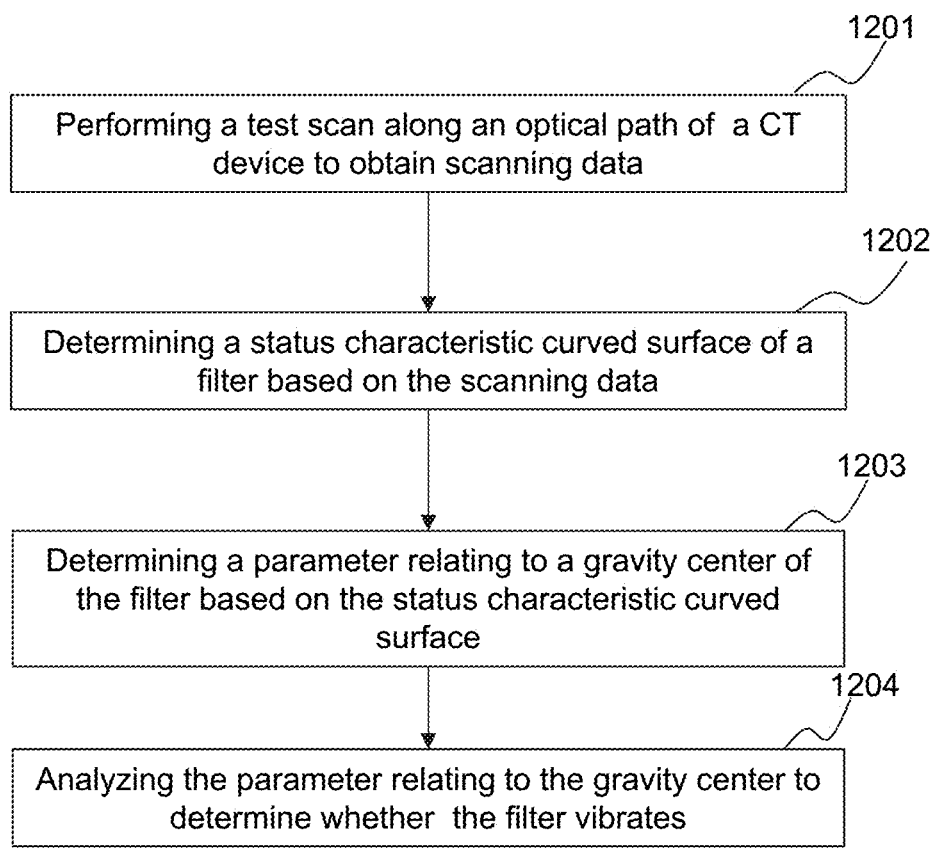
FIG. 12 shows the flowchart of an exemplary process for detecting whether the filter vibrates according to some embodiments of the present disclosure.

FIG. 12 shows the flowchart of an exemplary process for detecting whether the filter vibrates. As shown in the figure, in step 1201, one or more test scans may be performed along the optical path of the CT system 100 to obtain first test scanning data In some embodiments, the controller 140 may control the ray source 131 to perform the test scan(s), and the obtaining unit 601 may obtain the scanning data. In step 1202, a status characteristic curved surface of the filter may be determined based on the first test scanning data. In some embodiments, the status characteristic curved surface is determined by the status characteristic index unit 602. In some embodiments, the details of step 1201 and step 1202 are the same as those of step 1001 and step 1002 of the previous embodiments, which are not repeated here. In some embodiments, the test scan may be a scan of a rotating gantry.

In step 1203, the gravity center related parameter of the filter may be determined based on the status characteristic curved surface. In some embodiments, the gravity center related parameter may be obtained by determining the geometric center of the filter in the channel and a slice direction for each view of the rotation test scan. In some embodiments, the status characteristic index unit 602 may obtain the gravity center related parameter based on the status characteristic curved surface. In step 1204, the gravity center related parameter may be analyzed to determine whether the filter vibrates. In some embodiments, a threshold of a deviation of the gravity center related parameter may be pre-determined. When the maximum deviation or the average deviation of the gravity center related parameter exceeds the threshold, it is determined that the filter vibrates.

In some embodiments, the threshold may include an upper threshold and a lower threshold. In some embodiments, the analysis-determination unit 603 may analyze the gravity center related parameter to determine whether the filter vibrates.

It should be noted that the above description of the process for detecting whether the filter of the CT system 100 vibrates is merely exemplary, and is not intended to limit the present application to the scope of the embodiments. It should be understood by those skilled in the art that, after understanding the process, various amendments and changes in forms and details of the application fields of implementing the above method and system may be realized while the function is realized, which is within the protection scope of the present application.

Figure 13:
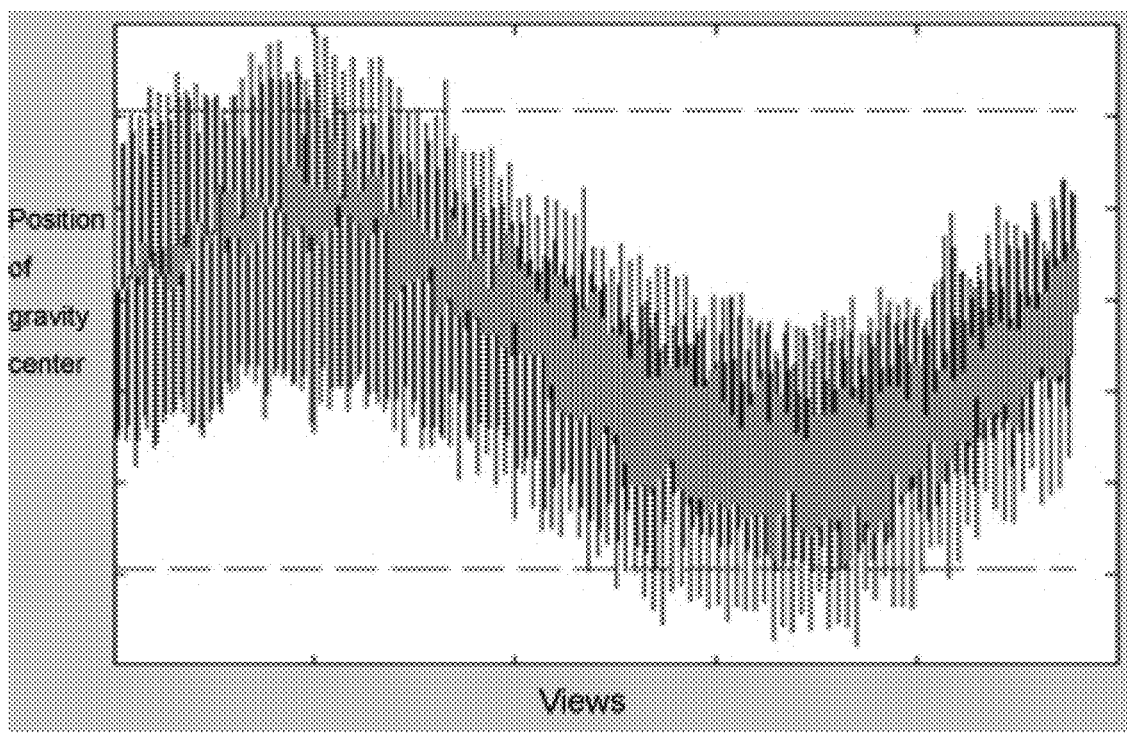
FIG. 13 shows experimental data obtained from examples of detecting whether the filter vibrates according to some embodiments of the present disclosure.

FIG. 13 shows exemplary gravity center related parameters of the filter obtained from a method for detecting whether the filter vibrates. The abscissa represents different views, and the ordinate represents the position of gravity center. When the filter does not vibrate, the positions of gravity center in different views are fixed; i.e., it should be a straight line parallel to the horizontal axis; and when the filter vibrates, the gravity centers of the filter in various views may not overlap with each other, and a curve, for example, that shown in FIG. 13 may occur. Therefore, it is determined that the filter vibrates when the maximum deviation or the average deviation of the gravity center of the filter in each view exceeds a certain threshold; and it is determined that the filter does not vibrate when deviations of the gravity center of the filter in each view do not exceed the certain threshold. In some embodiments, the threshold may include an upper threshold and a lower threshold. In some embodiments, the determination is performed by the analysis-determination unit 603 of the optical path detection module 510.

Figure 14:
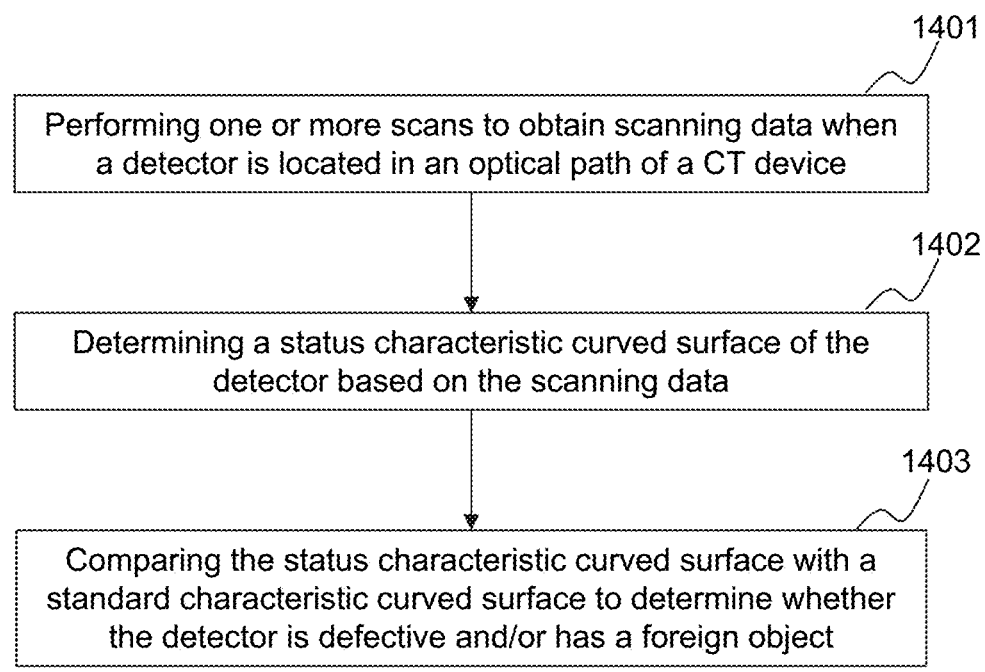
FIG. 14 shows the flowchart of an exemplary process for detecting whether the detector is defective or has a foreign object according to some embodiments of the present disclosure.

FIG. 14 shows an exemplary process for detecting whether the detector is defective or has a foreign object. As shown in the figure, in step 1401, the CT system 100 may perform one or more test scans along the optical path of the CT system 100 when the detector is located in the optical path. In some embodiments, the controller 140 may control the ray source 131 to perform one or more test scans. The mode of the test scans may be a static scan or a rotating scan. In the rotating scan mode, data of the test scan in each view is averaged. In order to increase accuracy, the data of different test scans may be obtained by repeatedly performing test scans under different conditions, and the data of the test scans is comprehensively considered. For example, two test scans may be performed on two focal spots to obtain data of the detector at the two focal spots, and a status characteristic curved surface is determined based on the difference between the scanning data of the two test scans. Alternatively, a fly-focal spots scan may be performed to obtain data of two focal spots, and a status characteristic curved surface is determined based on the difference between the scanning data of the two test scans. As another example, two test scans may be performed on the air and the object 201 to be scanned separately to obtain the scanning data of the two test scans, and a status characteristic curved surface may be determined based on the difference between the scanning data of the two test scans. Here, the object 201 to be scanned is preferably a phantom, and the phantom is preferably a relatively thick uniform phantom to increase the radiation hardness. As another example, two test scans may be performed under different energies to obtain the scanning data of the two test scans, and a status characteristic curved surface may be determined based on the difference between the scanning data of the two test scans. Obviously, those skilled in the art may also select other scanning conditions to obtain data of different test scans. Here, the difference may be determined by subtracting the scanning data of the two test scans or dividing the scanning data of the two test scans.

In step 1402, a status characteristic curved surface of the detector may be determined based on the data of the test scan. In some embodiments, the status characteristic index unit 602 may determine the status characteristic curved surface of the detector based on the data of the test scan. In some embodiments, the scanning data of the two test scans obtained in step 1001 may be divided to obtain the status characteristic curved surface of the detector. In some embodiments, the status characteristic curved surface may be determined based on the difference between the first scan scanning data and the second scanning data. Those skilled in the art may also select other scanning conditions to obtain data of different test scans. Here, the difference may be determined by subtracting the scanning data of the two test scans or dividing the scanning data of the two test scans.

In step 1403, the status characteristic curved surface may be compared with a standard characteristic curved surface to determine whether the detector is defective and/or has a foreign object. In some embodiments, the analysis-determination unit 603 may compare the status characteristic curved surface with the standard characteristic curved surface to determine whether the detector is defective and/or has a foreign object. For example, whether the difference between the status characteristic curved surface and the standard characteristic curved surface exceeds a certain threshold may be determined: if yes, the detector may be defective (or may have a foreign object); and if no, the detector may be not defective (or may have no foreign object). In some embodiments, the processor 150 may compare the status characteristic curved surface with the standard characteristic curved surface to determine whether the detector is defective and/or has a foreign object.

In some embodiments, the comparison of the status characteristic curved surface and the standard characteristic curved surface may be performed by comparing each point on the status characteristic curved surface with each point on the standard characteristic curved surface, and whether the detector is defective or has a foreign object may be determined based on whether the difference corresponding to a point exceeds a threshold. In some embodiments, the threshold may include an upper threshold and a lower threshold. In some embodiments, the standard characteristic curved surface may be obtained and stored in advance (for example, stored in the storage unit 604). For example, steps 1401 and 1402 are performed in advance in a state where the detector is confirmed to be not defective and has no foreign object, and an obtained characteristic curved surface may be taken as the standard characteristic curved surface. Alternatively, the standard characteristic curved surface may be obtained immediately after step 1402 by smoothing the status characteristic curved surface.

It should be noted that the above description of the process for detecting whether the detector of the CT system 100 is defective and/or has a foreign object is merely exemplary, and is not intended to limit the present application to the scope of the embodiments. It should be understood by those skilled in the art that, after understanding the process, various amendments and changes in forms and details of the application fields of implementing the above method and system may be realized while the function is realized, which is within the protection scope of the present application.

Figure 15:
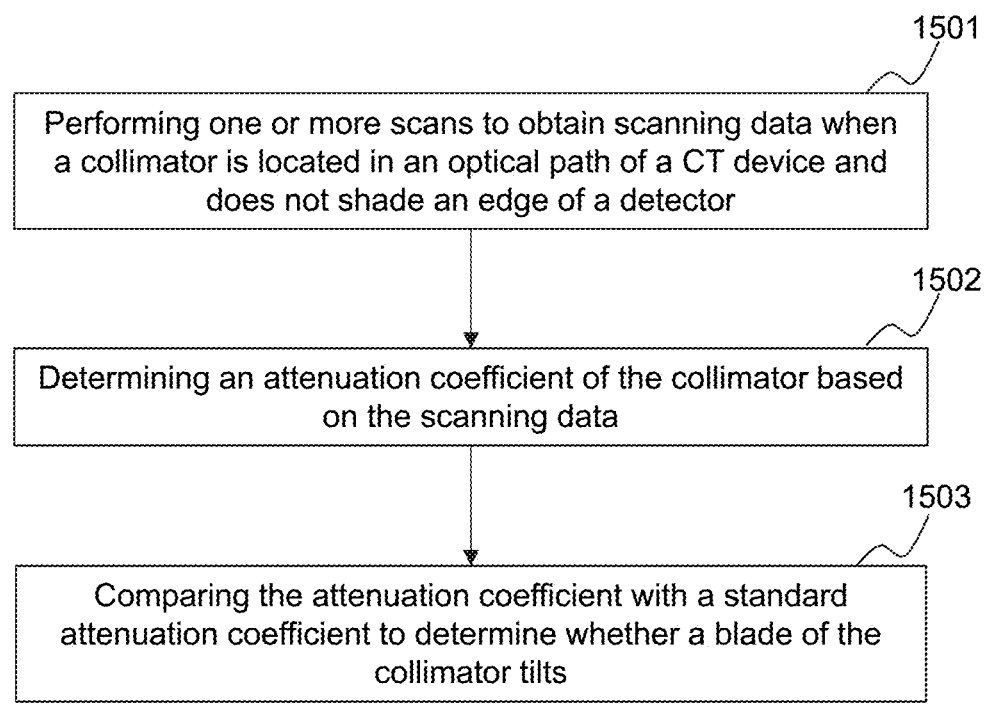
FIG. 15 shows the flowchart of an exemplary process for detecting whether a collimator tilts according to some embodiments of the present disclosure.

FIG. 15 shows an exemplary process for detecting whether a collimator tilts. As shown in the figure, in step 1501, the CT system 100 may perform one or more test scans along the optical path of the CT system 100 when the collimator is located in the optical path and does not shade the edge of a detector. In some embodiments, the mode of the scans may be a static scan or a rotating scan. Since the collimator does not shade the edge of the detector, the collimator may not shade a row of the edge of the detector. In order to eliminate the error, the data of different test scans may be obtained by repeatedly performing test scans under different conditions, and the data of the test scans may be comprehensively considered. For example, one or more rotation test scans may be performed by the CT system 100 where the collimator is not located in the optical path and does not shade a row of the edge of the detector at all, to obtain second test scanning data. In some embodiments, the controller 140 may control the ray source 131 to perform the test scans.

In step 1502, an attenuation coefficient of the collimator may be determined based on the data of the test scan. In some embodiments, the attenuation coefficient of the collimator may be determined based on the difference between the first test scanning data and the second test scanning data. Those skilled in the art may also select other scanning conditions to obtain data of different test scans. Here, the difference may be determined by subtracting the scanning data of the two test scans or dividing the scanning data of the two test scans. In some embodiments, the status characteristic index unit 602 may determine the attenuation coefficient of the collimator.

In step 1503, the attenuation coefficient may be compared with a standard attenuation coefficient to determine whether a blade of the collimator tilts. In some embodiments, whether the difference between the attenuation coefficient and the standard attenuation coefficient exceeds a certain threshold may be determined: if yes, the collimator tilts; and if no, the collimator does not tilt. In some embodiments, the threshold may include an upper threshold and a lower threshold. In some embodiments, the analysis-determination unit 603 may compare the attenuation coefficient with the standard attenuation coefficient to determine whether the collimator tilts. In some embodiments, the standard attenuation coefficient may also be obtained and stored in advance (for example, stored in the storage unit 604). For example, steps 1501 and 1502 are performed in advance in a state where the collimator is confirmed not to tilt, and an obtained attenuation coefficient may be taken as the standard attenuation coefficient.

It should be noted that the above description of the process for detecting whether the collimator of the CT system 100 tilts is merely exemplary, and is not intended to limit the present application to the scope of the embodiments. It should be understood by those skilled in the art that, after understanding the process, various amendments and changes in forms and details of the application fields of implementing the above method and system may be realized while the function is realized, which is within the protection scope of the present application.

Figure 16:
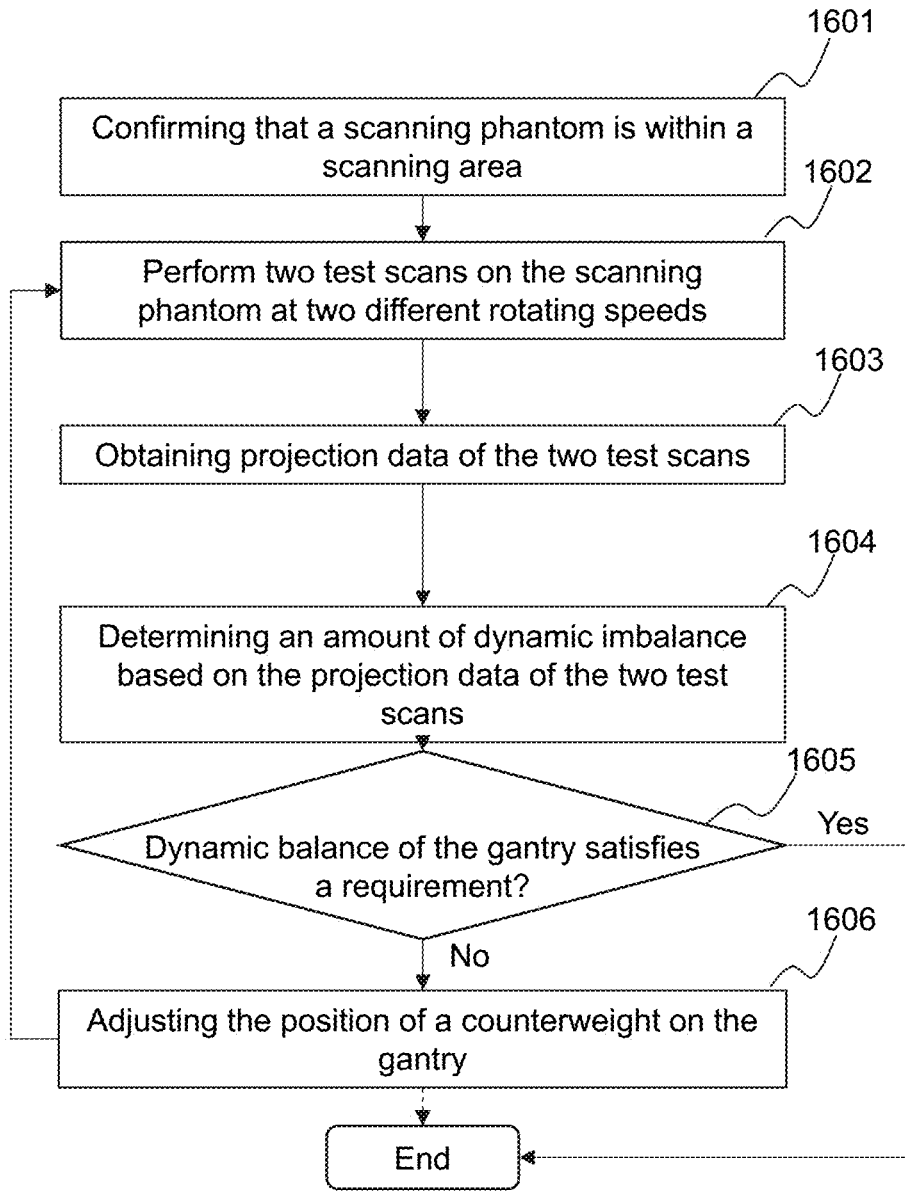
FIG. 16 shows the flowchart of an exemplary process for adjusting a dynamic balance of a gantry according to some embodiments of the present disclosure.

According to some embodiments of the present application, FIG. 16 shows an exemplary process for adjusting a dynamic balance. As shown in the figure, in step 1601, an object 201 to be scanned may be confirmed within a scanning area. In some CT systems 100, the object 201 to be scanned may be determined to be within the scanning area by a positioning slice scanning, and in some CT systems 100, the object 201 to be scanned may be determined to be within the scanning area by laser positioning.

In step 1602, two test scans may be performed on the object 201 to be scanned at two different rotating speeds. In some embodiments, a high-speed test scan and a low-speed test scan may be performed on the object 201 to be scanned. For example, the speed of the high-speed test scan may be the maximum rotating speed that the CT system 100 can achieve. In some embodiments, the speed of the high-speed test scan may be set to 4 rev/s (for example, the rotor rotates 4 revolutions per second), and the speed of the low-speed test scan may be set to 0.5 rev/s (for example, the rotor rotates half a revolution per second). In some embodiments, the controller 140 may control the ray source 131 to perform the test scans.

In step 1603, the projection data of the two test scans may be obtained. In some embodiments, the projection data in each view of the rotor rotating a revolution relating to the two test scans may be obtained separately. In some embodiments, the obtaining unit 701 of the dynamic balance detection module 520 may obtain the projection data by the detector 132 of the CT system 100.

In step 1604, an amount of dynamic imbalance may be determined based on the projection data of the two test scans. In some embodiments, the dynamic imbalance amount unit 702 of the dynamic balance detection module 520 may determine the amount of dynamic imbalance. Take a simple motion model as an example; when the rotor 130 of the gantry 110 does not reach a full dynamic balance, the ray source 131 may vibrate back and forth in the Z-axis direction during high-speed rotation, and the period is one revolution. Accordingly, the projection position (position in the Z-axis direction) of the object 201 to be scanned on the detector 132 also moves with the rotating angle, and the period is one revolution. In some embodiments, the amount of dynamic imbalance may be represented by the deviation of the projection position of the object 201 to be scanned on the detector. In some embodiments, the projection positions of the object 201 to be scanned may be obtained based on the projection data (scanning data) of the two test scans, and the deviation is the difference in projection positions of the two test scans.

In step 1605, whether the dynamic balance of the gantry satisfies a requirement may be determined based on the amount of dynamic imbalance. In some embodiments, a threshold may include an upper threshold and a lower threshold. In some embodiments, the analysis-determination unit 703 of the dynamic balance detection module 520 may determine whether the dynamic balance of the gantry satisfy a requirement. If yes, the adjustment is finished; and if no, step 1606 is performed. In some embodiments, a threshold of the deviation may be determined in advance. It is determined that the dynamic balance of the gantry does not satisfy the requirement when the rotor rotates for a revolution, and the difference between the maximum deviations or average deviations of the projection positions exceed the threshold. In some embodiments, the console 160 may provide a feedback regarding the amount of dynamic imbalance or a determined result obtained in step 1605 to the user, and the user may decide whether to perform a further adjustment. In step 1606, the position of the counterweight (s) 202 on the gantry 110 may be adjusted based on the amount of dynamic imbalance. In some embodiments, the console 160 may provide a feedback regarding the amount for the counterweight(s) 202 that needs to be adjusted and is obtained in step 1606 to the user, and the user may decide whether to perform a further adjustment. In some embodiments, an adjustment mode and an amount that needs to be adjusted of the counterweight(s) 202 may be determined by the processor 150 of the CT system 100, and the position(s) of the counterweight(s) 202 may be adjusted by the controller 140. A more specific description can be found elsewhere in the present disclosure.

Returning to step 1602, a test scan may be performed again, and an amount of dynamic imbalance may be determined; if the amount of dynamic imbalance does not satisfy the requirement, the counterweight 202 is adjusted again until the dynamic imbalance of the gantry 110 satisfies the requirement.

It should be noted that the above description of the process for detecting the dynamic balance of the gantry of the CT system 100 is merely exemplary, and is not intended to limit the present application to the scope of the embodiments. It should be understood by those skilled in the art that, after understanding the process, various amendments and changes in forms and details of the application fields of implementing the above method and system may be realized while the function is realized, which is within the protection scope of the present application. For example, in some embodiments, step 1606 of adjusting the position of the counterweight(s) 202 may be performed before step 1605 of determining whether the dynamic imbalance satisfies a requirement; step 1601 may be omitted; and step 1604 of obtaining projection data and step 1605 of determining an amount of dynamic imbalance may be combined as one step.

Figure 17:
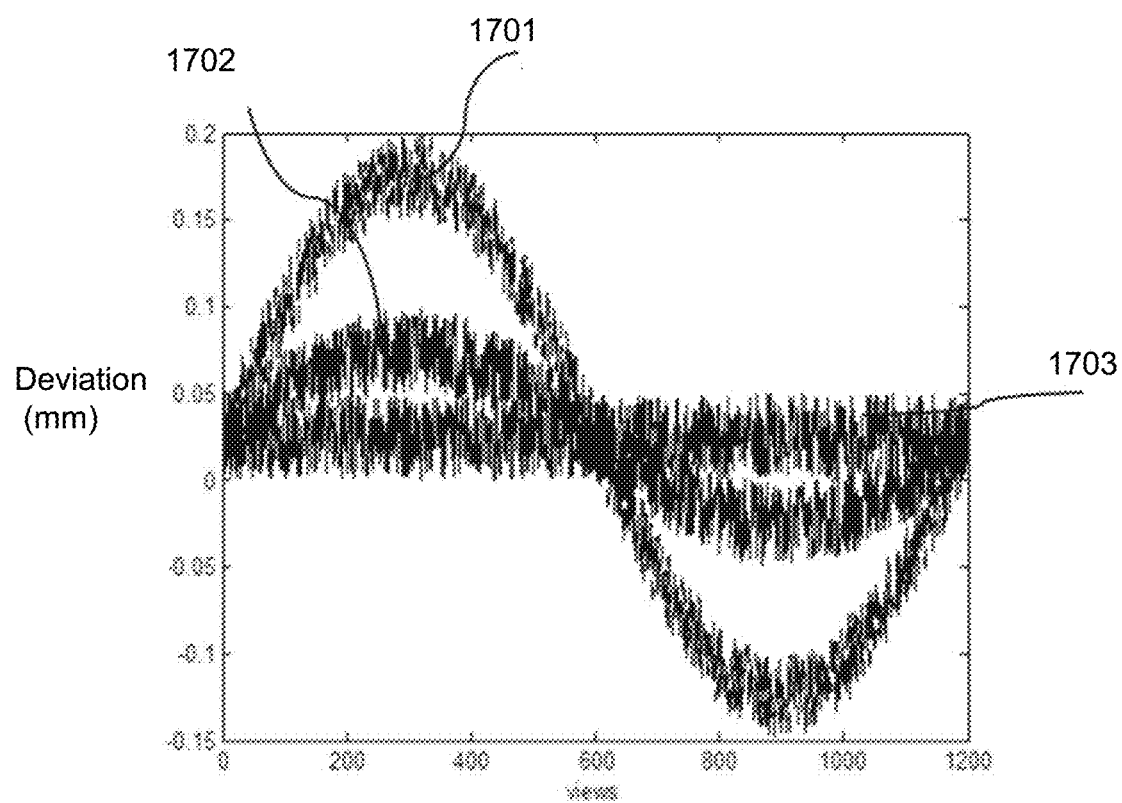
FIG. 17 shows an exemplary comparison chart of dynamic balance of the gantry before and after being adjusted by a method for adjusting dynamic balance of the gantry according to some embodiments of the present disclosure.

FIG. 17 is an exemplary comparison chart of the dynamic balance of the gantry before and after being adjusted by a method for adjusting the dynamic balance of the gantry of the CT system 100 according to some embodiments. The abscissa represents different views (phase). The rotor is rotated for a revolution to obtain projection position in 1200 different views. The ordinate is deviations of the projection positions of the trajectory of the object 201 to be scanned (for example, a steel ball) in different views. The projection positions may be obtained based on the projection data, and the deviation of the projection position may represent an amount of dynamic imbalance of the gantry (a degree of vibration when the rotor rotates). Curve 1701 represents the deviations of the projection position before adjustment, curve 1702 represents deviations of the projection position after one time of adjustment, and curve 1703 represents time deviation of the projection position after two times of adjustment. As shown in FIG. 17, after the position(s) of the counterweight(s) 202 is adjusted twice by using the measuring and adjusting method according to the present application, the amount of dynamic imbalance of the gantry is obviously decreased.

It should be noted that the above description of the process for detecting the status of the optical path is merely for convenience of descriptions and is not intended to limit the present application to the scope of the embodiments. It should be understood by those skilled in the art that, after understanding the principle of the process, various amendments and changes in forms and details of the application fields of implementing the above process and system may be realized without departing from this principle while the function is realized, which is within the protection scope of the present application. These amendments and changes are still within the scope of the above description. For example, in some embodiments, the detection of the status of the optical path is not limited to the determination of the above-described components (e.g., the filter, the collimator, and the detector), and other components (e.g., the ray source) in the optical path of the CT system 100 may also be used, as long as a status thereof may be indicated in the scanning data. Accordingly, the status characteristic index may be determined based on characteristics of the optical path components.

As described above, the optical path components may include the ray source, the detector, or a component between the ray source and the detector during the test scan.

Since the ray source is configured to emit a radiation beam, if there is abnormity (e.g., defects, having a foreign object, tilting, or vibrating) in the ray source, it will result in different attenuation of the beam for at least two scans. The attenuation of the beam may be reflected in the scanning data of the at least two scans. Accordingly, the status of the ray source may be indicated in the scanning data, and a status characteristic index reflecting the attenuation of the beam may be determined based on the scanning data, thereby detecting whether there is abnormity in the ray source.

Therefore, the above description of the process for detecting the status of the optical path may be also applicable for detecting the status of the ray source, e.g., detecting whether the ray source is abnormal. For example, a status characteristic index of the ray source may be determined by determining a difference between the scanning data of at least two scans, and the determination of whether the ray source is abnormal may be made by comparing the status characteristic index with an index threshold. In response to determining that the status characteristic index exceeds the index threshold, a determination that the ray source is abnormal may be obtained.

In some embodiments, the abnormity of the ray source may include defects, having a foreign object, tilting, or vibrating. The abnormity of having a foreign object may include that there is a gas (e.g., one or more bubbles) or a part fallen off the tube in the oil in the tube of the ray source, or that there is other foreign object in the ray source.

Figure 18:
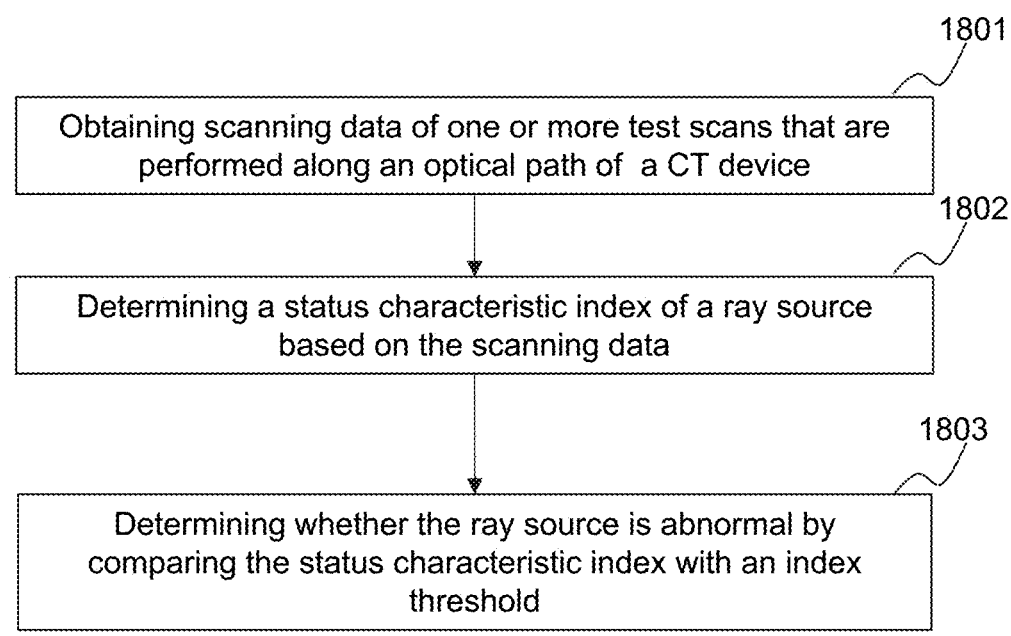
FIG. 18 shows a flowchart of an exemplary process for detecting whether a ray source is abnormal according to some embodiments of the present application.
Figure 19:
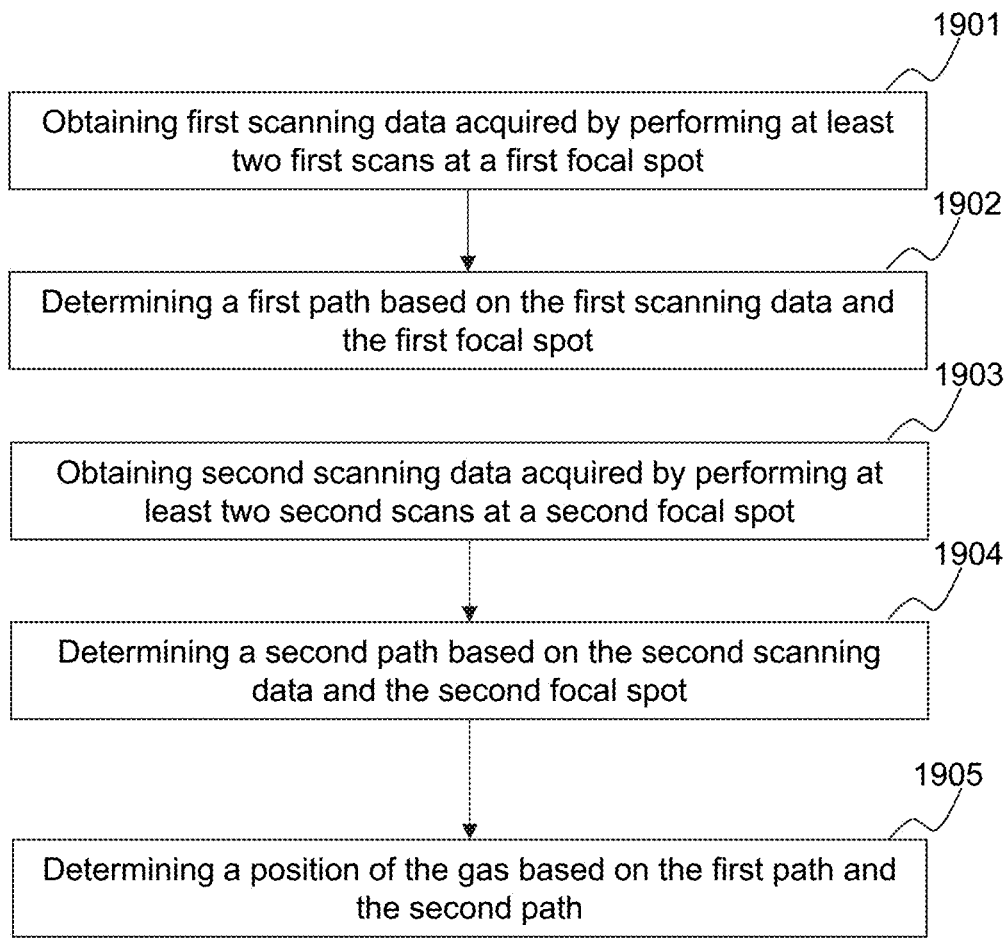
FIG. 19 shows a flowchart of an exemplary process for determining a position of a gas in oil of a tube of a ray source according to some embodiments of the present application.

For brevity, the following description of FIG. 18 and FIG. 19 may take the abnormity that a gas exists in the oil in the tube of the ray source as an example. It should be noted that for persons having ordinary skills in the art, the process described in FIG. 18 and FIG. 19 may be applied to other similar situations, such as the ray source is tilt, the ray source vibrates, or the ray source has other foreign object. Alternatively or additionally, the processes described in FIGS. 8-15 may also be applied to determining whether the ray source is abnormal.

According to some embodiments of the present application, FIG. 18 shows a flowchart of an exemplary process for detecting whether a ray source is abnormal. In some embodiments, the process 1800 may be implemented in the system 100 illustrated in FIG. 1. For example, the process 1800 may be stored in a storage device as a form of instructions, and invoked and/or executed by a processing device (e.g., the processor 150). The operations of the illustrated process presented below are intended to be illustrative. In some embodiments, the process 1800 may be accomplished with one or more additional operations not described, and/or without one or more of the operations discussed. Additionally, the order in which the operations of the process 800 as illustrated in FIG. 18 and described below is not intended to be limiting.

In 1801, the processor 150 may obtain scanning data of at least two scans. The at least two scans may be performed along the optical path of the CT system 100 to obtain the data of the at least two scans (e.g., the scanning data).

In some embodiments, the at least two scans may be performed on the air or an object. Here, the object is preferably a phantom, and the phantom is preferably a relatively thick uniform phantom to increase the radiation hardness.

In some embodiments, the mode of the scan may be a static scan or a rotating scan. For example, the at least two scans may be static scans in which the at least two scans are performed under a same gantry angle. As another example, the at least two scans may be rotating scans in which the at least two scans are performed under at least two gantry angles. For each scan, data of the scan in each gantry angle is averaged to obtain the scanning data of the scan.

In some embodiments, a scanning condition may include at least one of: a position of a focal spot of the ray source, energy of the plurality of rays, an object to be scanned, a rotating speed relating to a rotating scan, or a position of the ray source. In some embodiments, the at least two scans may be perform red under the same condition. In some embodiments, in order to eliminate the error, the at least two scans may be performed under different scanning conditions, and the data of the at least two scans is comprehensively considered. For example, two scans may be performed on two focal spots to obtain data of the detector at the two focal spots. Alternatively, a fly-focal spots scan may be performed to obtain data of two focal spots. As another example, two scans may be performed under different energies of rays (e.g., different electric currents and/or different electric voltages of the ray source) to obtain the scanning data of the two scans. Obviously, those skilled in the art may also select other scanning conditions to obtain data of different scans.

In some embodiments, the controller 140 may control the ray source 131 to perform the at least two scans, and the processor 150 (e.g., the obtaining unit 601) may obtain the scanning data.

In some embodiments, the scanning data of a scan may include a plurality of projection values each of which is output by one of a plurality of detecting units of the detector.

In some embodiments, in order to increase contrast of the scanning data, the at least two scans may be performed at a relatively low electric voltage, e.g., less than 100 kV.

In 1802, the processor 150 may determine a status characteristic index of the ray source based on the scanning data.

In some embodiments, the processor 150 may determine a difference between the scanning data of the at least two scans as the status characteristic index of the ray source.

If there is foreign object in the oil of the tube of the ray source, since the foreign object in the oil may move, it will result in different attenuation of the rays of different scans, so through the different attenuations of the optical paths of the at least two scans, it is possible to detect whether there is a foreign object in the ray source. If other foreign object appears in the oil, it will cause an increase in the attenuation of rays. If a gas appears in the oil, the attenuation of rays will decrease. Therefore, if a decrease in the attenuation of rays is detected, it is generally considered to be caused by an abnormity that there is a gas in the oil of the tube of the ray source. The scanning data includes the projection values detected by the detector, which can reflect the attenuation of rays, so the change of the attenuation can be reflected according to the difference of the scanning data of the at least two scans.

In 1803, the processor 150 may determine whether the ray source is abnormal by comparing the status characteristic index with an index threshold.

In some embodiments, the processor 150 may determine a difference of projection values that are detected by the same detecting unit but in different scans. The difference of projection values corresponding to a detecting unit may be referred to as a status characteristic index corresponding to the detecting unit. The processor 150 may compare the status characteristic index corresponding to each detecting unit with the index threshold. In response to determining that the status characteristic index exceeds the index threshold, the processor 150 may determine that there is a gas (e.g., one or more bubbles) in the oil of the tube of the ray source, e.g., in a path between the focal spot of the ray source and the detecting unit.

In some embodiments, the processor 150 may determine an average of the differences of projection values corresponding to the plurality of detecting units. The processor 150 may compare the average with the index threshold. In response to determining that the average exceeds the index threshold, the processor 150 may determine that there is a gas in the oil of the tube of the ray source.

In some embodiments, for a scan, the processor 150 may determine a distribution of the projection values detected by the plurality of detecting units. The processor 150 may determine a difference of the distributions of the at least two scans. The processor 150 may compare the distribution difference with the index threshold. In response to determining that the distribution difference exceeds the index threshold, the processor 150 may determine that there is a gas in the oil of the tube of the ray source.

In some embodiments, for a scan, the processor 150 may determine a gravity center (or mass center) of the distribution of the projection values detected by the plurality of detecting units. The processor 150 may determine a difference of the gravity centers (or mass centers) of different test scans. The processor 150 may compare the gravity center difference with the index threshold. In response to determining that the gravity center difference exceeds the index threshold, the processor 150 may determine that there is a gas in the oil of the tube of the ray source.

In some embodiments, the difference of the scanning data of the at least two scans may be determined by subtracting the scanning data of the at least two scans or dividing the scanning data of the at least two scans.

It should be noted that the above description is merely for convenience of descriptions and is not intended to limit the present application to the scope of the embodiments. It should be understood by those skilled in the art that, after understanding the principle of the process, various amendments and changes in forms and details of the application fields of implementing the above process and system may be realized without departing from this principle while the function is realized, which is within the protection scope of the present application. These amendments and changes are still within the scope of the above description.

According to some embodiments of the present application, FIG. 19 shows a flowchart of an exemplary process for determining a position of a gas in the oil of the tube of the ray source. In some embodiments, the process 1900 may be implemented in the system 100 illustrated in FIG. 1. For example, the process 1900 may be stored in a storage device as a form of instructions, and invoked and/or executed by a processing device (e.g., the processor 150). The operations of the illustrated process presented below are intended to be illustrative. In some embodiments, the process 1900 may be accomplished with one or more additional operations not described, and/or without one or more of the operations discussed. Additionally, the order in which the operations of the process 1900 as illustrated in FIG. 19 and described below is not intended to be limiting. In some embodiments, after determining that there a gas in the oil of the tube of the ray source in the process 1800, the processor 150 may perform the process 1900 to further determine the position of the gas in the oil.

In 1901, the processor 150 may obtain first scanning data acquired by performing at least two first scans at a first focal spot.

In 1902, the processor 150 may obtain second scanning data acquired by performing at least two second scans at a second focal spot.

In 1903, the processor 150 may determine, based on the first scanning data and the first focal spot, a first path.

In 1904, the processor 150 may determine, based on the second scanning data and the second focal spot, a second path.

In some embodiments, the at least two first scans and the at least two second scans may be perform at the same gantry angle.

In some embodiments, at least two first scans may be performed at the first focal spot but at different electric currents and/or electric voltages. In some embodiments, at least two first scans may be performed at the first focal spot with other parameters being the same.

In some embodiments, the processor 150 may determine, based on the first scanning data, a difference of projection values that are detected by the same detecting unit but in different first scans. The processor 150 may compare the difference corresponding to each detecting unit with the index threshold. In response to determining that the difference exceeds the index threshold, the processor 150 may determine the first path between the first focal spot of the ray source and the detecting unit.

The determination of the second path is similar to the determination of the first path, which is not repeated here.

In some embodiments, a fly-focal spots scan may be performed to obtain data of two focal spots.

In 1905, the processor 150 may determine a position of the gas in the oil of the tube of the ray source based on the first path and the second path.

In some embodiments, the processor 150 may determine a point of intersection between the first path and the second path as the position of the gas in the oil.

In some embodiments, the processor 150 may determine a first position difference between the first focal spot and the second focal spot. The processor 150 may determine a second position difference between the detecting unit corresponding to the first path and the detecting unit corresponding to the second path. The processor 150 may determine a magnification ratio between the first position difference and the second position difference. The processor 150 may determine the position of the gas in the optical path between the ray source and the detector based on the magnification ratio and the distance between the ray source and the detector.

In some embodiments, if there is no point of intersection between the first path and the second path, the processor 150 may determine a segment that connects the first path and the second path, and indicates the shortest distance between the first path and the second path. The processor 150 may determining a point (e.g., the midpoint) in the segment as the position of the gas in the oil.

In some embodiments, the processor 150 may determine more than two paths, and determine the position of the gas based on the one or more points of intersection of the more than two paths. For example, if there are two or more points of intersection of the more than two paths, the processor 150 may determine the average position of the two or more points of intersection as the position of the gas.

In some embodiment, if there are a plurality of bubbles in the oil, the process 150 may determine a position for each bubble according to the process 1900.

In some embodiments, the processor 150 may notify a user (e.g., a doctor, an operator, an engineer, a technician, etc.) of the system 100 that there a gas in the oil of the tube of the ray source and/or notify the user the position of the gas. The form of the notification may include text, image, voice, video, or the like, or any combination thereof.

It should be noted that the above description is merely for convenience of descriptions and is not intended to limit the present application to the scope of the embodiments. It should be understood by those skilled in the art that, after understanding the principle of the process, various amendments and changes in forms and details of the application fields of implementing the above process and system may be realized without departing from this principle while the function is realized, which is within the protection scope of the present application. These amendments and changes are still within the scope of the above description.

The method for measuring and adjusting a status of an optical path and a dynamic balance of a gantry in the CT system 100 according to the embodiments of the present application may be implemented by a computer-readable medium, for example, computer software, hardware, or a combination of computer software and hardware. For the hardware implementation, the embodiments described in the present application may be implemented by one or more application specific integrated circuits (ASICs), digital signal processors (DSPs), digital signal processing devices (DAPDs), programmable logic devices (PLDs), field programmable gate arrays (FPGAs), processors, controllers, microcontrollers, microprocessors, other electronic devices performing the above-described functions, or selected combinations of the above. In some cases, the embodiments may be implemented by a controller.

In the above, the CT scan apparatus that can use the image reconstruction method provided by the present application has been described by way of example only. Those skilled in the art should understand, for example, a device such as a C-arm system using X-rays, a combinational medicine imaging system (e.g., Positron Emission Tomography-Computed Tomography, PET-CT), or a tomographic imaging apparatus using other types of radiation can be applied to CT reconstruction methods and devices described in the present application. The type and structure of the computed tomography devices are not limited in the present application. Although the present application has been disclosed in the above-preferred embodiments, it is not intended to limit the present application. Any person skilled in the art can make some modifications and improvements without departing from the spirit and scope of the present application. The scope of protection is defined by the claims.

What is claimed is:

1. A system comprising:
   at least one storage device including a set of instructions; and
   at least one processor configured to communicate with the at least one storage device, wherein when executing the set of instructions, the at least one processor is configured to direct the system to perform operations including:
   obtaining scanning data obtained from at least two scans that are performed by a medical device, the medical device including a ray source configured to generate a plurality of rays and a detector configured to detect the plurality of rays;
   determining, based on a difference of the scanning data, a status characteristic index of the ray source; and
   determining whether abnormity exists in a tube of the ray source based on the status characteristic index, includes:
   determining whether a foreign object exists in the tube of the ray source based on the status characteristic index.

2. The system of claim 1, wherein determining, based on a difference of the scanning data, a status characteristic index of the ray source includes:
   for each of a plurality of detecting units of the detector, determining, in the scanning data of the at least two scans, a difference of projection values detected by the detecting unit; and
   determining the difference or an average of the differences of the projection values corresponding to the detecting unit as the status characteristic index corresponding to the detecting unit.

3. The system of claim 1, wherein determining, based on a difference of the scanning data, a status characteristic index of the ray source includes:
   for each of the at least two scans, determining, based on the scanning data corresponding to the scan, a distribution of projection values detected by a plurality of detecting units;
   determining a difference of the distributions of the at least two scans; and
   determining the difference of the distributions as the status characteristic index.

4. The system of claim 1, wherein determining, based on a difference of the scanning data, a status characteristic index of the ray source includes:
   for each of the at least two scans,
   determining, based on the scanning data corresponding to the scan, a distribution of projection values detected by a plurality of detecting units;
   determining a gravity center of the distribution;
   determining a difference of the gravity centers of the at least two scans; and
   determining the difference of the gravity centers as the status characteristic index.

5. The system of claim 1, wherein the at least two scans are performed at a same gantry angle of the medical device.

6. The system of claim 1, wherein determining whether abnormity exists in the tube of the ray source based on the status characteristic index includes:
   comparing the status characteristic index with an index threshold;
   in response to determining that the status characteristic index exceeds the index threshold, determining that abnormity exists in the tube of the ray source.

7. The system of claim 6, wherein the at least one processor is configured to direct the system to perform the operations including:
   obtaining first scanning data acquired by performing at least two first scans at a first focal spot of the ray source;
   determining, based on the first scanning data and the first focal spot, a first path;
   obtaining second scanning data acquired by performing at least two second scans at a second focal spot of the ray source;

determining, based on the second scanning data and the second focal spot, a second path; and determining a position of the abnormality based on the first path and the second path.

8. The system of claim 7, wherein the at least two first scans or the at least two second scans are performed at different electric currents or different electric voltages.

9. A method implemented on a machine including one or more processors and one or more storage devices, comprising:

obtaining a first scanning data obtained from a first scan and a second scanning data obtained from a second scan that are performed by a medical device, the medical device including a ray source configured to generate a plurality of rays and a detector configured to detect the plurality of rays;

determining, based on a difference between the first scanning data and the second scanning data, a status characteristic index of the ray source; and determining whether abnormity exists in a tube of the ray source based on the status characteristic index, includes:

determining whether a foreign object exists in the tube of the ray source based on the status characteristic index.

10. The method of claim 9, wherein determining, based on a difference between the first scanning data and the second scanning data, a status characteristic index of the ray source includes:

for each of a plurality of detecting units of the detector, determining, in the first scanning data and the second scanning data, a difference of projection values detected by the detecting unit; and determining the difference or an average of the differences of the projection values corresponding to the detecting unit as the status characteristic index corresponding to the detecting unit.

11. The method of claim 9, wherein determining, based on a difference between the first scanning data and the second scanning data, a status characteristic index of the ray source includes:

for each of the first scan and the second scan, determining, based on the scanning data corresponding to the scan, a distribution of projection values detected by a plurality of detecting units;

determining a difference of the distributions of the first scan and the second scan; and determining the difference of the distributions as the status characteristic index.

12. The method of claim 9, wherein determining, based on a difference between the first scanning data and the second scanning data, a status characteristic index of the ray source includes:

for each of the first scan and the second scan,
determining, based on the scanning data corresponding to the scan, a distribution of projection values detected by a plurality of detecting units;

determining a gravity center of the distribution;
determining a difference of the gravity centers of the first scan and the second scan; and
determining the difference of the gravity centers as the status characteristic index.

13. The method of claim 9, wherein the first scan and the second scan are performed at a same gantry angle of the medical device.

14. The method of claim 9, wherein determining whether abnormity exists in the ray source based on the status characteristic index includes:

comparing the status characteristic index with an index threshold;

in response to determining that the status characteristic index exceeds the index threshold, determining that abnormity exists in the ray source.

15. The method of claim 14, wherein the at least one processor is configured to direct the system to perform the operations including:

obtaining first scanning data acquired by performing the first scan at a first focal spot of the ray source;

determining, based on the first scanning data and the first focal spot, a first path;

obtaining second scanning data acquired by performing the second scan at a second focal spot of the ray source;

determining, based on the second scanning data and the second focal spot, a second path; and determining a position of the abnormality based on the first path and the second path.

16. A non-transitory computer readable medium, comprising at least one set of instructions, wherein when executed by one or more processors of a computing device, the at least one set of instructions causes the computing device to perform a method, the method comprising:

obtaining scanning data obtained from a first scan and a second scan that are performed by a medical device, the medical device including a ray source configured to generate a plurality of rays and a detector configured to detect the plurality of rays;

determining, based on a difference between the first scanning data and the second scanning data, a status characteristic index of the ray source; and determining whether abnormity exists in a tube of the ray source based on the status characteristic index, includes:

determining whether a foreign object exists in the tube of the ray source based on the status characteristic index.

17. The system of claim 1, wherein the abnormity includes at least one of a defect or tilting.

18. The system of claim 1, wherein determining whether a foreign object exists in the tube of the ray source based on the status characteristic index includes:

determining whether a gas exists in oil of the tube of the ray source based on the status characteristic index.

19. The system of claim 18, wherein determining whether a gas exists in oil of the tube of the ray source based on the status characteristic index includes:

determining a change of attenuation of rays in the at least two scans based on the difference of the scanning data of the at least two scans; and in response to determining that a decrease in the attenuation of rays is detected in the at least two scans, determining that a gas exists in the oil of the tube of the ray source.

* * * * *